United States Patent [19]
Koller et al.

[11] Patent Number: 5,426,036
[45] Date of Patent: Jun. 20, 1995

[54] PROCESSES FOR THE PREPARATION OF FOREIGN PROTEINS IN STREPTOMYCETES

[75] Inventors: Klaus-Peter Koller, Bad Soden am Taunus; Günther Riess, Frankfurt am Main; Eugen Uhlmann, Glashütten/Taunus; Holger Wallmeier, Bad Soden am Taunus, all of Germany

[73] Assignee: Hoechst Aktiengesellschaft, Germany

[21] Appl. No.: 30,731

[22] Filed: Mar. 12, 1993

Related U.S. Application Data

[63] Continuation-in-part of Ser. No. 687,610, Apr. 19, 1991, abandoned, Ser. No. 430,622, Nov. 1, 1989, abandoned, and Ser. No. 735,757, Jul. 29, 1991, abandoned, which is a continuation of Ser. No. 189,840, May 3, 1988, abandoned.

[30] Foreign Application Priority Data

| Date | Country | Number |
|---|---|---|
| May 5, 1987 [DE] | Germany | 37 14 866.4 |
| Nov. 3, 1988 [DE] | Germany | 38 37 273.8 |
| Aug. 19, 1989 [DE] | Germany | 39 27 449.7 |
| Apr. 21, 1990 [DE] | Germany | 40 12 818.0 |

[51] Int. Cl.[6] .......................................... C12N 15/62
[52] U.S. Cl. ............................. 435/69.7; 435/252.3; 435/320.1; 536/23.4
[58] Field of Search ............... 435/69.7, 252.3, 320.1; 530/350; 536/27, 23.4

[56] References Cited

U.S. PATENT DOCUMENTS

| | | | |
|---|---|---|---|
| 4,366,246 | 12/1982 | Riggs | 435/69.7 |
| 4,411,994 | 10/1983 | Gilbert et al. | |
| 4,717,666 | 1/1988 | Brawner et al. | |
| 4,918,007 | 4/1990 | Koller et al. | 435/69.2 |

FOREIGN PATENT DOCUMENTS

| | | |
|---|---|---|
| 0161629 | 5/1985 | European Pat. Off. |
| 0177827A2 | 4/1986 | European Pat. Off. |
| 0195691 | 9/1986 | European Pat. Off. |
| 0281090 | 9/1988 | European Pat. Off. |
| 0289936A2 | 11/1988 | European Pat. Off. |
| 0290005A2 | 11/1988 | European Pat. Off. |
| 0292763 | 11/1988 | European Pat. Off. |
| 0367163A2 | 5/1990 | European Pat. Off. |
| 85/3672 | 12/1985 | South Africa |
| WO88/02005 | 3/1988 | WIPO |
| WO91/03550 | 3/1991 | WIPO |

OTHER PUBLICATIONS

Koller et al., Bio/Technology 7:1055–1059 (1989).
Koller et al., J. Bacteriology 171(9):4953–4957 (1989).
Vertesy et al., Eur. J. Biochem. 141:505–512 (1984).
Suggs et al., PNAS USA 78(11):6613–6617 (1981).
Brawner, et al., Expression Systems, CC 036, UCLA Symp. Suppl. 14A p. 103 (1990).
Shang Chang, Methods in Enzymology 153:507–516 (1987).
Noack et al., Gene 68:53–62 (1988).
PNAS 83:6766–6770, Sep. 1986, This ex. of Secretion and processing of insulin precursors in yeast.

*Primary Examiner*—Garnette D. Draper
*Assistant Examiner*—John D. Ulm
*Attorney, Agent, or Firm*—Finnegan, Henderson, Farabow, Garrett & Dunner

[57] ABSTRACT

The tendamistat gene can be used for the construction of fused genes with which fusion proteins are expressed and excreted in Streptomycetes host cells. The tendamistat portion can be modified, in particular it can be C-terminal shortened. When a gene for a shortened proinsulin in which the insulin B chain is linked to the A chain only via Lys or Lys-Lys is coupled to the tendamistat gene, this gene construction is introduced into an expression vector, and the latter is used to transform a Streptomycetes host cell, there is expression and secretion of the corresponding fusion protein. The fusion protein can easily be cleaved to give insulin precursors because of correctly established disulfide bonds. Genetic structures which code for the signal sequence and about the first ten amino acids of tendamistat as well as a desired protein are expressed in streptomyces host cells with a high yield, and the fusion proteins are secreted into the medium.

27 Claims, 5 Drawing Sheets

5,426,036

PROCESSES FOR THE PREPARATION OF FOREIGN PROTEINS IN STREPTOMYCETES

This application is a continuation in part of U.S. patent application Ser. No. 07/687,610, filed Apr. 19, 1991, now abandoned; and U.S. patent application Ser. No. 07/430,622, filed Nov. 1, 1989, now abandoned; and U.S. patent application Ser. No. 07/735,757, filed Jul. 29, 1991, now abandoned, which is a continuation of the U.S. patent application Ser. No. 07/189,840, filed May 3, 1988, now abandoned. All of these U.S. patent applications are hereby specifically incorporated by reference herein.

BACKGROUND AND SUMMARY OF THE INVENTION

The European patent application with the publication number (EP-A) 0,161,629, and South African Patent 85/3672 disclose the use of the DNA coding for the signal peptide (prepeptide) of the α-amylase inhibitor tendamistat in order for a Streptomycetes cell to excrete a polypeptide, in particular tendamistat. In this regard, South African Patent No. 85/3672 at page 2, lines 24–30, teaches that the signal peptide of tendamistat is Met-Arg-Val-Arg-Ala-Leu-Arg-X-Ala-Ser-Ala in which X represents a hydrophobic region comprising 10 to 25, preferably 17 to 20 amino acids (most likely 20 amino acids) (SEQ ID NO:48). The appropriate DNA can, in principle, be obtained from every strain producing tendamistat, but a DNA obtained as in Example 3 of German Offenlegungsschrift 3,331,860 is preferably used. German Patent Application P 37 07 150.5, filed Mar. 6, 1987, has already proposed a process for the excretion of fusion proteins from Streptomycetes, which comprises incorporating the coding sequence, which has been modified where appropriate, and expressing the recombinant gene in a Streptomycetes cell. Thus, in this case the tendamistat structural gene is used as a "carrier" for another gene, the fusion proteins which are obtained having the amino acid sequence of another protein located within the tendamistat amino acid sequence. Consequently, on chemical or enzymatic cleavage of this fusion protein to liberate the other protein, two tendamistat part-sequences are obtained. Said German patent application P 37 07 150.5 also relates to tendamistat derivatives, which are understood to include those with a markedly shortened amino acid chain. Derivatives of this type are able in a reversible manner to react with the specific receptors in the form of a competitive inhibitory mechanism.

In the European patent application with the publication number (EP-A) 0,289,936 which corresponds to the German patent application DE 37 14 866 A1, now issued as German patent P 37 14 866.4, the inventors of the present application disclose the production of fusion proteins by coupling the structural gene for the desired protein to the 3'-end of the coding strand of the optionally modified tendamistat gene, expressing this genetic structure in a streptomyces host cell and isolating the secreted fusion protein from the supernatant. In a preferred embodiment the tendamistat gene is truncated at the 3'-end. For the truncation, the cleavage sites for the restriction enzyme BstEII in the region of triplets 31 and 32, StuI in the region of triplets 43 and 44, and Sau3A in the region of triplets 52 and 53 are used.

The present inventors have found that foreign proteins can also be prepared in Streptomycetes by constructing fusion protein genes in which the structural gene for the desired protein is coupled in the 3' end (of the coding strand) of the tendamistat gene, which has been modified where appropriate. The modification of the tendamistat gene may comprise, in particular, C-terminal shortening.

The DNA coding for tendamistat is depicted in EP-A 0,161,629 (where it is DNA sequence C (Table 1 in the annex of the present application)) (SEQ ID NO: 40). This structural gene contains several cleavage sites for restriction enzymes, which can be used to modify the coded amino acid sequence. Suitable cleavage sites are those for BstEII in the region of triplets 31 and 32, StuI in the region of triplets 43 and 44, and Sau3A in the region of triplets 52 and 53. It is possible, by incorporation of appropriate linkers, to insert at these sites one or more additional amino acids, to eliminate DNA segments between these cleavage sites, or to code for shortened amino acid sequences by incorporation of stop codons. Furthermore, it is possible by site-specific mutagenesis for any desired amino acids to be inserted, replaced or eliminated. In this way proteins are obtained which have an α-amylase inhibitory action, as well as proteins which do not have this activity but still react with the corresponding receptors.

The invention also relates to appropriate gene structures, vectors containing these gene structures, Streptomycetes cells transformed with these vectors, the excreted fusion proteins, and their use for the preparation of the foreign proteins and tendamistat derivatives.

In a further embodiment of the present invention, the present inventors have found that the process of the present invention can be used particularly well to prepare a fusion protein in which tendamistat portion is followed by a shortened proinsulin whose C chain comprises only one or two lysine residues ("mini-proinsulin"). These precursors can be converted particularly straightforwardly and economically into human insulin. Further embodiments of the invention include truncating the tendamistat portion, too, in fusion proteins of this type (EP-A 0,367,163 published on May 9, 1990).

Further embodiments of the present invention relate to advantageous gene structures and processes for the amplification and expression of the gene which codes for the fusion protein.

Surprisingly, the present inventors have discovered that fusion proteins with a very short tendamistat portion are stable in Streptomyces cells and are secreted into the medium. The fusion proteins obtained in this way behave like "mature" proteins because of the very short tendamistat chain. The present inventors have also discovered that fusion proteins containing a tendamistat portion and a C-terminal portion of a proinsulin derivative in which the B chain is connected to the A chain via a bridging member comprising Lys or Lys-Lys are, in fact, unexpectedly stable and are secreted into the medium, from which they can be isolated in high yields. Surprisingly, tendamistat mini-proinsulin derivatives characterized by an unnaturally short C-peptide are always secreted with correctly established disulfide bonds whereas tendamistat fusion proteins containing a authentic proinsulin moiety are secreted with incorrect disulfide linkages. This unique feature of tendamistat "mini-proinsulin" derivatives allows easy enzymatic cleavage to yield human insulin derivatives.

BRIEF DESCRIPTION OF THE DRAWINGS

FIG. 1 shows the preparation of the hybrid plasmid pKK310 which codes for a fusion protein in which part of the tendamistat amino acid sequence is followed by a bridging member of seven amino acids and, thereafter, the amino acid sequence of monkey proinsulin.

FIG. 2 shows the construction of the expression plasmid pTF1 starting from the plasmid pkk310.

FIG. 3 shows the construction of the plasmid pRS10 in which part of the tendamistat gene is followed by the polylinker from pUC18, and its reconstruction into the expression plasmid pTF10. "mcs" denotes the polylinker region (multiple cloning site) of pUC18.

FIG. 4 shows the construction of the plasmid pKK400 which codes for a fusion protein in which the whole of the amino acid sequence of tendamistat is followed by a bridging member of eleven amino acids and, thereafter, the amino acid sequence of monkey proinsulin, and its reconstruction into the expression plasmid pGF1.

FIG. 5 shows the construction of the plasmid pKK500 as described in Example 6.

Figure 1:
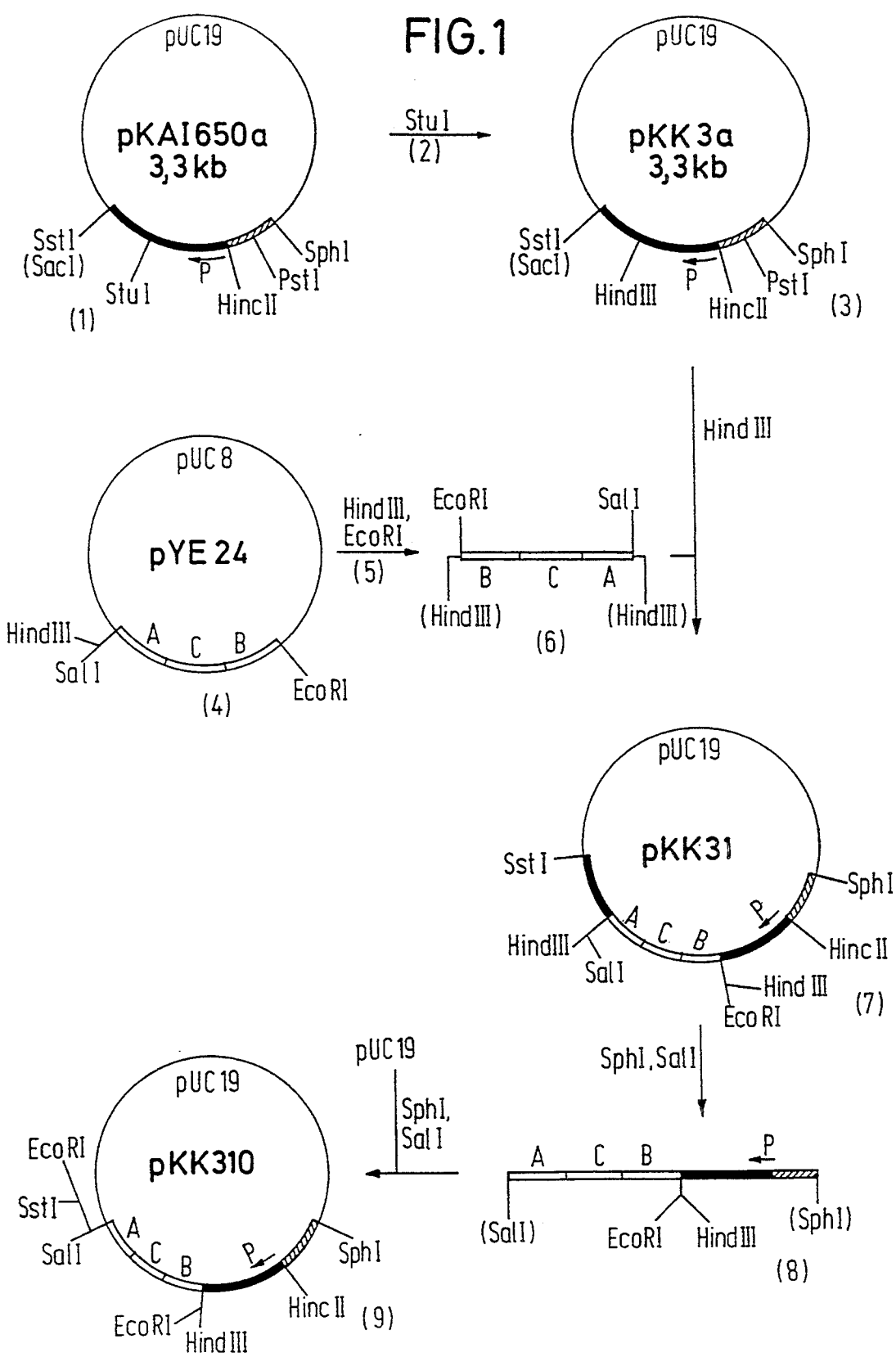
FIGS. 1 to 5 depict some plasmid constructions according to the invention.

The figures are not drawn true to scale.

DETAILED DESCRIPTION OF THE INVENTION

All the references discussed below are specifically incorporated by reference herein.

EP-A 0,177,827 discloses a synthetic signal sequence for transporting proteins in expression systems, wherein the DNA is virtually identical to a natural signal sequence but has one or more cleavage sites for endonucleases, which are not contained in the natural DNA. It is possible to produce eukaryotic, prokaryatic or viral proteins in prokaryatic and eukaryotic cells, by fusing the gene for the desired protein to a DNA signal sequence (described above), incorporating the fusion gene into a vector, and transforming a host cell which transports the expressed protein out of its cytoplasm. Using the periplasmic protein alkaline phosphatase as an example, it is shown that it is advantageous in the expression in *E. coli* to place the codons for about the first 40 amino acids of alkaline phosphatase immediately downstream of the pre-sequence and upstream of the structural gene for the desired protein. However, in many cases even fewer additional amino acids are sufficient, for example about 10, preferably about 5. About 90% of a corresponding fusion protein with simian proinsulin was transported into the periplasmic space. However, it has not been shown that the three disulfide linkages in the proinsulin moiety of the fusion protein were formed in the correct manner (Koller, K. P. et al. (1989) BIO/-TECHNOLOGY Vol. 7, 1055–1059; Koller K. P. et al. (1991) Genetics and Product Formation in Streptomyces, 227–233).

It has also been proposed (WO 91/03550, published Mar. 21, 1991) to produce fusion proteins by constructing a mixed oligonucleotide which codes for the ballast portion of the fusion protein, introducing this oligonucleotide into a vector in such a way that it is functionally coupled to a regulatory region and the structural gene for the desired protein, transforming suitable host cells with this plasmid population obtained in this way and selecting those clones which show a high yield of coded fusion protein. The oligonucleotide preferably consists of 4 to 12, in particular 4 to 8, triplets in this case.

It has already been attempted to produce fusion proteins with a short ballast portion. Thus, a gene fusion which codes for a fusion protein from the first 10 amino acids of β-galactosidase and somatostatin has, for example, been produced. However, it became apparent that this short β-galactosidase fragment was not sufficient to protect the fusion protein from digestion by endogenous host proteases (US-A 4,366,246, column 15, paragraph 2).

Accordingly, fusion proteins whose ballast portion consists of a β-galactosidase fragment having more than 250 amino acids are described in EP-A 0,290,005 and 0,292,763.

However, the present inventors have discovered that fusion proteins with an N-terminal portion of tendamistat, preferably with about the first 10 amino-terminal amino acids of tendamistat, and a desired protein, for example a proinsulin, are, in fact, unexpectedly stable and are secreted into the medium, from which they can be isolated in high yields. Surprisingly, this is also true for relatively small proteins such as "mini-proinsulins". "Mini-proinsulin" refers to a truncated proinsulin.

"About 10 amino acids" is intended to mean in this case that even fewer amino acids are suitable, for example the first 7 N-terminal amino acids of tendamistat, but preferably not more than 10. Fusion proteins in whose tendamistat portion proline is present in position 7 and-/or 9 (as in the natural sequence) are preferred. However, it is, of course, possible to choose a larger tendamistat ballast portion in accordance with the embodiments already known or proposed, the advantage of low "ballast" being lost more and more, of course.

Particularly advantageous fused constructions can be readily determined by simple preliminary experiments if the concept of the invention is known.

It is furthermore possible to realize the concept of the invention also in other Gram-positive bacterial cells, for example in bacillus or staphylococcus cells using signal sequences which are "recognized" by these hosts.

The fusion proteins obtained according to the invention are present in the medium in a dissolved form, which has many advantages in processing and purification. Thus, enzymatic processing with cleaving of the ballast portion can, for example, take place directly on the secretion product, and working-up steps, such as the ones necessary for insoluble fusion proteins, do not have to be carried out. It is possible and even advantageous to vary the natural amino acid sequence of the tendamistat portion, i.e. to exchange or delete amino acids, or to insert amino acids which do not occur in the natural amino acid sequence. Furthermore, it is possible to vary the amino acid sequence in the signal peptide. It is also possible to carry out concentration or purification processes, for example affinity chromatography but also ultrafiltration, precipitation, ion exchange chromatography, adsorption chromatography, gel filtration or high-pressure liquid chromatography, first, before further processing.

The fusion proteins obtained according to the invention, which are exported from the cell, have the advantage that they can readily be isolated from the culture filtrate. The isolation can be carried out in a manner known per se, advantageously by adsorption or ion exchange chromatography and/or gel filtration or by direct crystallization after enrichment of the culture fluid, for example, by ultrafiltration.

The desired foreign protein (fusion partner) is liberated by enzymatic or chemical cleavage likewise in a manner known per se.

In this connection, the type of cleavage depends, in particular, on the amino acid sequence of the desired protein. It will be expedient in many cases to incorporate a connecting member or bridging member in the cleavage site between the tendamistat sequence and the amino acid sequence of the desired protein. If the desired protein contains, for example, no methionine, the connecting member can denote Met, whereupon chemical cleavage with cyanogen chloride or bromide is carried out. If the connecting member has a carboxyl-terminal cysteine, or if the connecting member represents Cys, it is possible for enzymatic cysteine-specific cleavage, or chemical cleavage, for example after specific S-cyanylation, to follow. If the bridging member has a carboxyl-terminal tryptophan, or if the connecting member represents Trp, chemical cleavage with N-bromosuccinimide can be carried out.

Desired proteins which do not contain Asp-Pro in their amino acid sequence and are sufficiently stable to acid can, as fusion proteins having this bridging member, be cleaved proteolytically in a manner known per se. This results in proteins which contain N-terminal proline and C-terminal aspartic acid. Thus, it is also possible in this way to synthesize modified proteins.

The Asp-Pro bond can be made even more labile to acid if this bridging member denotes $(Asp)_n$-Pro or is Glu-$(Asp)_n$-Pro, n denoting 1 to 3.

Examples of enzymatic cleavages have also been disclosed, it also being possible to use modified enzymes having improved specificity (cf. C. S. Craik et al., Science 228 (1985) 291–297). If the desired eukaryotic peptide is proinsulin, it is expedient to choose a peptide sequence in which an amino acid which can be eliminated by trypsin (Arg, Lys) is bonded to the N-Terminal amino acid (Phe) of the proinsulin, for example Ala-Ser-MEt-Thr-Arg, (SEQ ID NO: 1), since it is then possible to carry out the arginine-specific cleavage using the protease trypsin.

If the desired protein does not contain the amino acid sequence, (SEQ ID NO: 2):

Ile-Glu-Gly-Arg, the fusion protein having the corresponding bridging member can be cleaved with factor Xa (EP-A 0,025,190 and 0,161,973).

The isolation of the cleavage products depends on the properties of these proteins. Concerning the isolation of tendamistat and its derivatives, reference may be made to the literature cited in German Offenlegungsschrift 3,331,860.

The gene structure employed according to the invention is advantageously based on a synthetic gene which codes for the shortened proinsulin derivative. It is expedient in the construction of this gene to take account of the specific codon usage of Streptomycetes. It has emerged that the yield of fusion protein is thereby increased.

It is also advantageous to incorporate a terminator sequence in the synthetic gene structure, because an increase in the synthesis rate is also thereby achieved.

A great advantage of the process according to the invention comprises the possibility of detecting the fusion proteins using the plate test which is described in EP-A10,161,69 in Example 3 and in German Offenlegungsschrift 3,536,182. This considerably facilitates not only the selection of the interesting clones but also the working up because the effect of the different parameters on the yield can easily be established.

The fusion proteins obtained according to the invention are apparently present in a conformation which corresponds, or at least approximates, to that of mature insulin. This not only considerably facilitates the further processing to insulin but, moreover, at fermentation times long enough to provide a good yield, surprisingly there is only minimal attack by the proteases excreted into the fermentation medium.

The modification according to the invention of the proinsulin molecule with its shortened C chain permits straightforward processing to human insulin, namely by chemical cleavage with hydroxylamine and/or by enzymatic cleavage using trypsin or, advantageously, lysyl endoproteinases. Enzymatic cleavage is preferred. Lysyl endoproteinases carry out specific carboxyl-terminal cleavage after the amino acid lysine. The favorable arrangement of the A and the B chain in the fusion protein according to the invention means that the action of the said enzymes results in an insulin precursor in which, surprisingly, the disulfide bridges are correctly linked.

It is expedient in the construction of the gene to provide between the tendamistat portion and the start of the proinsulin molecule a bridging member which permits the proinsulin derivative to be cleaved off from the tendamistat portion with the same enzyme used to cleave the proinsulin derivative into the two insulin chains.

Cleavage of the fusion proteins according to the invention with a lysyl endopeptidase results—depending on the construction of the modified C chain-in de-$B^{30}$-insulin which can be transformed into human insulin by transpeptidation, or $B^{31}$-Lys-insulin or $B^{31}$-Lys-$B^{32}$-Lys-insulin, each of which can be transformed into human insulin, for example, by the use of carboxypeptidase B.

Particularly high yields of the desired protein are obtained when gene construction with a shortened tendamistat gene are employed. This embodiment of the process according to the invention has the great advantage that the portion of the modified insulin in the fusion protein comprises about one half, and thus contains considerably less "ballast". The correct folding of the fusion protein is not impaired by the shortening of the tendamistat portion, so that the advantageous working up is therefore also possible with the smaller fusion protein according to the invention. Nor is this advantage achieved at the expense of an increased rate of degradation by the proteases intrinsic to the host—in fact, unexpectedly, it has emerged that the stability to these proteases is increased.

The invention thus allows a whole series of advantageous gene constructions which result in insulin precursors which can easily be separated from the "ballast portion" of the fusion protein. This straightforward working up additionally improves the yield of human insulin.

The separation of the soluble fusion protein from the culture medium, its further processing to the insulin precursor and the transformation thereof into human insulin can be carried out by methods known per se. Thus, the fusion protein can advantageously be isolated by adsorption or ion exchange chromatography and/or gel filtration, and the proinsulin portion can be cleaved off chemically or, advantageously, enzymatically. The construction of appropriate bridging members is generally known and described, for example, in EP-A 0,229,998.

EP-B 0,089,007 discloses analogs of prepro- and proinsulin which carry at the C end of the prechain (or at the N-terminus of proinsulin) Lys or Arg (which is also preferred in the constructions according to the invention), whose B chain terminates with $B^{29}$-Lys and where the C peptide can be shortened to Lys or Arg so that therefore $B^{29}$-Lys in the proinsulin structure is, in the simplest case, followed by only Lys or Arg, to which the A chain is attached. These compounds are used as precursor for preparing insulins with the aid of trypsin or trypsin-like endopeptidases and of an ester of a natural amino acid which, where appropriate, carries protective groups.

Insulin precursors in which the B and A chain are connected by the bridging member -X-Y-, in which X and Y are identical or different and represent Lys and Arg, are disclosed in EP-A 0,195,691. These insulin precursors, however, are expressed from eucaryotic yeast and not from procaryotic bacteria and are then converted into human insulin by enzymatic transformation. Insulin precursors with a shortened C chain are also disclosed in EP-A 0,163,529. EP-B 0,132,769 and 0,132,770 describe insulin derivatives and pharmaceutical agents containing them.

According to certain preferred embodiments, the invention is explained in detail in the examples which follow. Unless otherwise indicated, percentage data relate to weight. FIGS. 1-4 relate to examples 1-4, respectively; FIG. 5 relates to Example 6.

EXAMPLE 1

The starting material used is the plasmid pKAI650, which is described in German Offenlegunsschrift 3,536,182 and in EP-A 0,218,204. This plasmid can be obtained from the plasmid pKAI1, which is described in German Offenlegungsschrift 3,331,860, by isolation of the 650 bp HincII/SstI fragment and cloning into the plasmid pUC19 which has been opened with these enzymes. The unique HindIII cleavage site in this plasmid is removed (by cutting with this enzyme, filling in the protruding ends, and ligation) to result in the plasmid pKAI650a (1).

2 µg of (1) DNA purified by CsCl gradient centrifugation are completely digested, in a 50 µl reaction mixture, with StuI for 2 hours as stated by the manufacturer, and the enzyme is removed by phenol extraction. The linearized DNA is precipitated with ethanol, redissolved and introduced into a ligation mixture to which is added, as additional reactant, 0.1 µg of the chemically synthesized double-stranded oligonucleotide (2) which has been phosphorylated at the 5' end, (SEQ ID NO: 3):

```
5'  C C C A A G C T T G G G  3'    (2)
3'  G G G T T C G A A C C C  5'
```

Transformation of the ligation mixture into *E. coli* JM 109 is followed by isolation of those clones which harbor the recombinant plasmid pKK3a (3). The isolated plasmid DNA has a cleavage site for the restriction enzyme HindIII, which permits characterization by restriction analysis. pKK3a (3) is 12 base-pairs larger than pKAI650a (1) and has a nucleotide sequence which extends the amino acid sequence by 4 amino acids, as follows, (SEQ ID NO: 4, amino acid sequence; SEQ ID NO: 5, nucleic acid sequence):

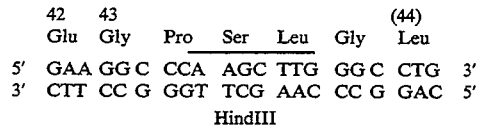
```
    42   43                        (44)
    Glu  Gly  Pro  Ser  Leu  Gly  Leu
5'  GAA  GGC  CCA  AGC  TTG  GGC  CTG  3'
3'  CTT  CC G  GGT  TCG  AAC  CC G  GAC  5'
                    HindIII
```

The other starting material used is the plasmid pYE24 (4). This plasmid is obtained by opening the vector pUC8 with EcoRI and HindIII, and ligating into this linearized plasmid the gene for monkey proinsulin (Table 2; cf. Wetekam et al., Gene 19 (1982) 179–183).

2 µg of the plasmid pYE24 (4) are reacted with the restriction enzymes EcoRI and HindIII, and the gene for monkey proinsulin is isolated by electroelution and, after purification and concentration by ethanol precipitation, it is ligated with the synthetic DNA linker (5), (SEQ ID NOS: 6 and 7):

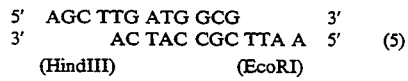
```
5'  AGC TTG ATG GCG         3'
3'           AC TAC CGC TTA A  5'    (5)
   (HindIII)       (EcoRI)
```

The ligation product (6) is now inserted into the plasmid PKK3a which has been opened with HindIII, resulting in the plasmid pKK31 (7). This construction results in the following bridging member being downstream of the codon for amino acid Gly 43 of the tendamistat gene, (SEQ ID NO: 8, amino acid sequence; and SEQ ID NO: 9, nucleic acid sequence):

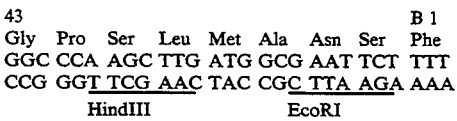
```
43                                        B 1
Gly  Pro  Ser  Leu  Met  Ala  Asn  Ser  Phe
GGC  CCA  AGC  TTG  ATG  GCG  AAT  TCT  TTT
CCG  GGT  TCG  AAC  TAC  CGC  TTA AGA  AAA
       HindIII              EcoRI
```

"B 1" here, and in Table 2, designates the start of the B chain of monkey proinsulin.

In plasmid (7) the proinsulin sequence is located within the tendamistat gene. To reconstruct this plasmid into a plasmid according to the invention, (7) is digested with SphI, and SalI, and the fragment (8) is isolated. The vector pUC19 is opened with SphI and SalI, and the linearized plasmid is ligated with the fragment (8). The resulting plasmid pKK310 (9) codes for a fusion protein in which the shortened tendamistat sequence and the linker which is depicted above are followed only by the proinsulin sequence.

The entire construction is depicted in FIG. 1.

EXAMPLE 2

To reconstruct the plasmid pKK310 (9) in an expression plasmid, (9) is reacted with SstI and SphI, and the fragment (10) is isolated.

The commercially available expression vector pIJ702 (11) (obtainable from the John Innes Foundation, Norwich, England) is opened with SphI and SstI, and the linearized plasmid (12) is ligated with the fragment (10). After transformation of the strain *Streptomyces Lividans* TK 24 (John Innes Foundation), the desired clones are identified by selection for resistance to thiostrepton. The plasmid DNA from thiostreptone-resistant clones is isolated and examined by restriction analysis. Plasmids having the desired orientation of the gene are called pTF1 (13). Clones which contain this recombinant plasmid secrete a protein of molecular weight 16 kD into the culture medium. This protein shows a positive "immunoblotting" reaction with insulin antibodies (cf. Example 5).

Figure 2:
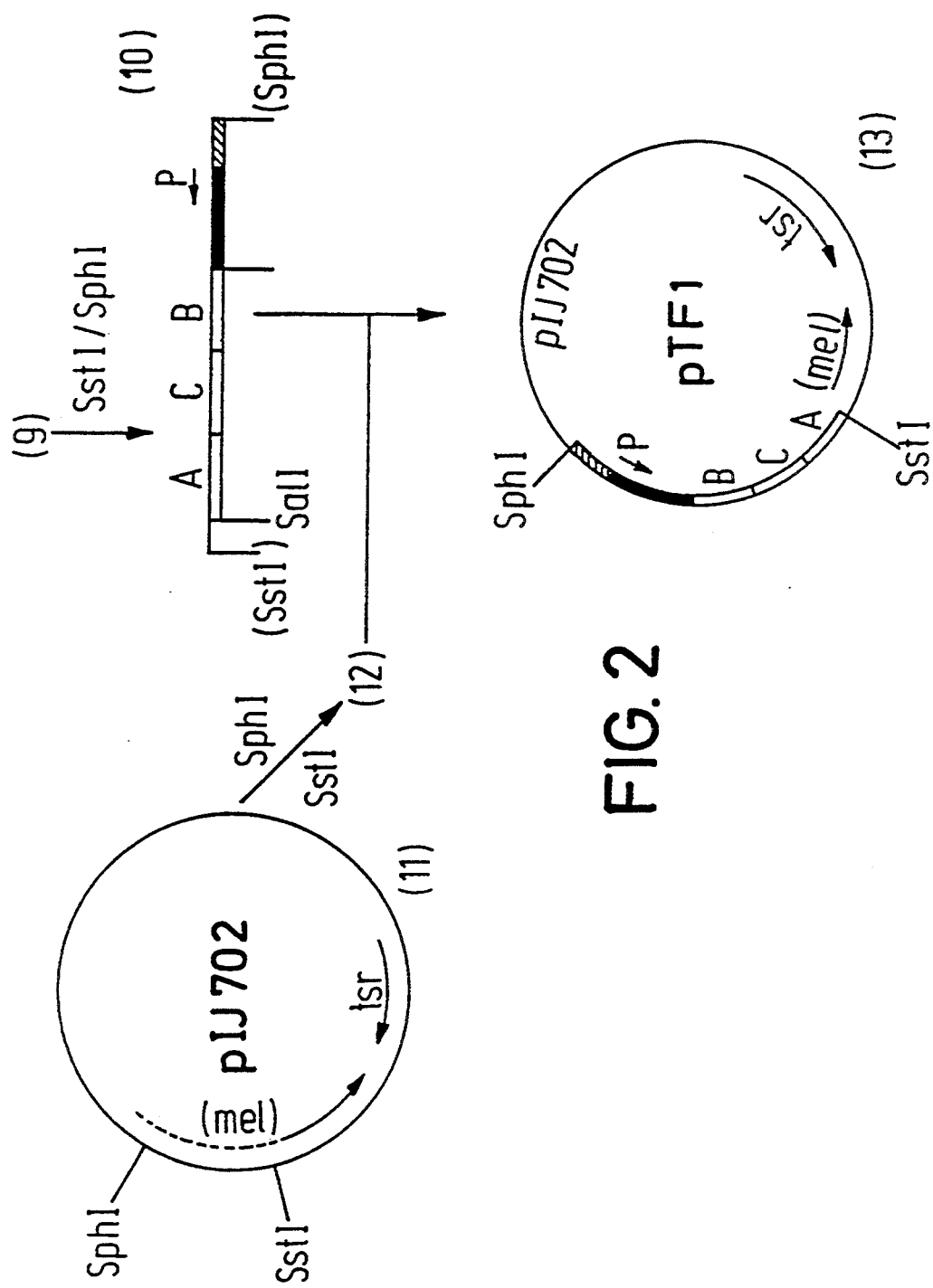

The construction of pTF1 (13) is depicted in FIG. 2.

EXAMPLE 3

The plasmid pKK3a (3), on the one hand, and the vector pUC18, on the other hand, are each opened with HindIII, and are ligated together. The ligation mixture is used to transform the *E. coli* strain JM 109, which indicates successful cloning in the presence of isopropyl-β-thio-galactopyranoside (IPTG) and 5-bromo-4-chloro-3-indolyl-β-D-glactopyranoside (X-Gal) by the formation of colorless colonies. The resultant recombinant plasmid pRS1 (14) is isolated in a manner known per se. Digestion of 1 μg of the plasmid with the restriction enzyme SstI, followed by religation results in deletion of the pUC18 portion apart from the polylinker sequence (mcs) and the remainder of the tendamistat gene. The plasmid pRS10 (15) is obtained.

The plasmid (15) is, owing to its polylinker portion, suitable for cloning any desired structural genes, resulting in plasmids which code for the corresponding fusion proteins with the shortened tendamistat sequence.

When pRS10 (15) is digested with SphI and SstI, and the smaller fragment is isolated, the latter can be ligated into the expression vector pIJ702 in analogy to Example 2. In this way the expression vector pTF10 (16) is obtained, and this likewise by reason of its polylinker portion, allows versatile constructions.

Figure 3:
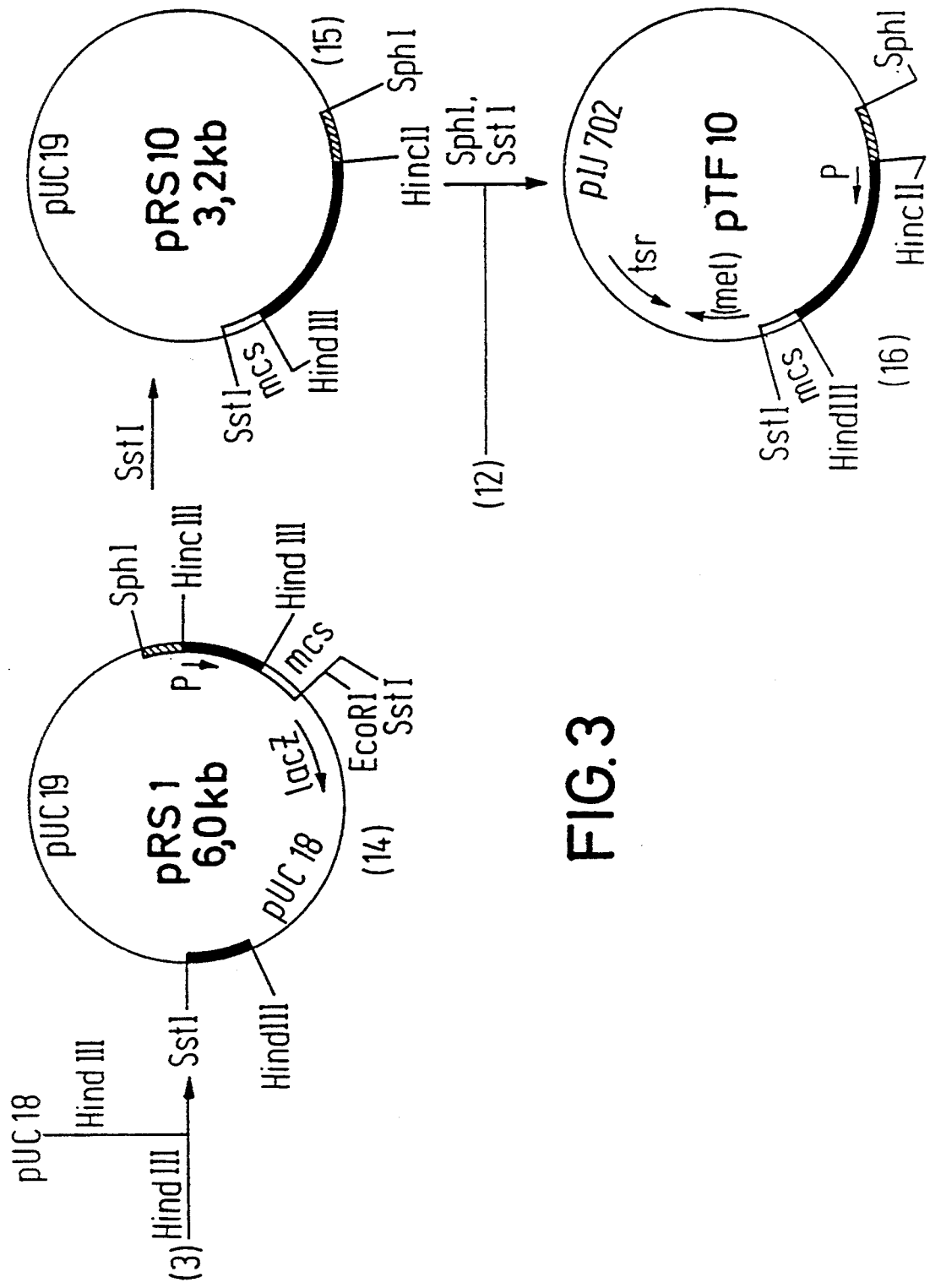

The construction of pTF10 (16) is depicted in FIG. 3.

EXAMPLE 4

The plasmid pYE24 (4) is opened with EcoRI, and the linker, (SEQ ID NOS: 10 and 11):

```
5'    AAT TCA AGC TTG        3'
3'            GT TCG AAC TTA A   5'
     (EcoRI)  Hind III  (EcoRI)
``` is inserted, resulting in the plasmid pYE241. Cutting with HindIII, and ligation into pKK3a (3) cut with HindIII results in the plasmid pKK32, in analogy to Example 1. The latter codes for a fusion protein in which the tendamistat sequence is linked to the proinsulin sequence by the following bridging member, (SEQ ID NO: 12, amino acid sequence; and SEQ ID NO: 13, nucleic acid sequence):

```
43
Gly Pro Ser Leu Asn Phe Ala Arg
GGC CCA AGC TTG AAT TCT GCA AGA TTT
CCG GGT TCG AAC TTA AGA CGT TCT AAA
```

In analogy to Example 1, pKK32 is cut with SphI and SstI, and the fragment which is approximately 650 bp in size is cloned into pUC19, which has been opened with these enzymes. The resulting plasmid pKK320 corresponds to plasmid pKK310 (9) apart from the above-mentioned bridging member (in which the sequence introduced by the linker is emphasized by emboldening).

In analogy to Example 2, the SstI-SphI fragment having the recombinant gene from pKK320 is cloned into pIJ702, resulting in the expression plasmid pTF2. A fusion protein of 16 kD is expressed and secreted in S. Lividans TK 24, and the protein reacts with insulin antibodies (cf. Example 5).

Because of the similarity of the construction of pTF2 to that of pTF1 (13), FIGS. 1 and 2, no depiction in a drawing has been given.

EXAMPLE 5 pkk310 (9) is partially digested with EcoRI so that only one of the two EcoRI cleavage sites is opened. After the protruding ends have been filled in using Klenow polymerase, the plasmid is religated, and the result is checked by restriction analysis. The desired plasmid, in which the EcoRI site located at the end of the proinsulin gene has been eliminated, is called pKK310a (17). Thus, the latter now contains a unique restriction site for EcoRI in the linker region between the shortened tendamistat gene and the proinsulin gene.

To construct the plasmid which codes for a fusion protein having the complete tendamistat sequence, a unique cleavage site for KpnI is introduced, in the region of the codons for amino acids 68/69, into the DNA sequence coding for tendamistat (Table 1). This entails the isolated DNA from pKAI650a (1) being digested with SstI and SphI, and the fragment which is 650 bp in size being cloned into the phage M13mp18 RF DNA, which has likewise been digested with these two enzymes, and the single-stranded DNA being prepared by known methods. 1 μg of this ssDNA is used together with 0.1 μg of the mutagenic "primer", (SEQ. ID NO: 14):

```
5' C GAG GTA CCG GGC GT 3'
``` in site-directed mutagenesis (M. J. Zoller and J. Smith, Nucleic Acid Res. 10 (1982) 6487–6500).

The RF DNA is isolated from the isolated M13 clones having the mutated gene, which can be selected by the additional KpnI cleavage site, and the base exchange (C for G at the third position in the codon for Arg[68]) is confirmed by sequencing. Thus, the nucleotide exchange brings about no change in the amino acid sequence but does introduce the desired new unique cleavage site into the tendamistat structural gene, (SEQ ID NO: 15, amino acid sequence; SEQ ID NO: 16, nucleic acid sequence):

```
 66   67   68   69   70
His  Ala  Arg  Tyr  Leu
CAC  GCC  CGC  TAC  CTC
GTC  CGG  GCC  ATC  GAG
              KpnI
```

The mutated sequence is, after SstI-SphI digestion, cloned out of the M13mp18 RF DNA into the plasmid pUC19, resulting in the plasmid pKAI651 (18).

To check, the 650 bp SStI-SphI insert from (18) is incorporated, as in Example 2, into the plasmid pIJ702, resulting in the plasmid pAX651. After this plasmid has been transformed into *Streptomyces Lividans* TK 24, the expression rates for tendamistat which are obtained are the same as for the plasmid pAX650 having the unmodified tendamistat gone (German Offenlegungsschrift 3,536,182, FIG. 3).

To prepare a plasmid, according to the invention, for a fusion protein having the entire amine acid sequence of tendamistat, the plasmid pKAI651 (18) is now digested with SphI and KpnI, and the small fragment is ligated with the linker (19) (with SEQ ID NOS. 18 and 19, nucleic acid sequence;SEQ ID NO: 17, amino acid sequence):

```
          69   70   71   72   73   74
       (Tyr)Leu  Ala  Arg  Cys  Leu  Phe  Asn  Ala  Met  Ala  Thr  Gly           3'
    5'       CTC  GCT  CGC  TGC  CTT  TTC  AAT  GCG  ATG  GCC  ACC  GGG
    3' C    ATG  GAG  CGA  GCG  ACG  GAA  AAG  TTA  CGC  TAC  CGG  TGG  CCC  TTA  A  5'
       (KpnI)                                                                  (EcoRI)
                                          (19)
``` and the plasmid pKK310a (17) which has been opened with SphI and EcoRI.

The ligation mixture is used to transform *E. coli* JM 109, the plasmid DNA is isolated, and the correct fusion is verified by DNA sequencing. The plasmid having the correct sequence is called pKK400 (20).

The Linker (19) codes not only for the remaining amine acids of tendamistat but also for the portion of a spacer which separates the tendamistat and proinsulin in genes from one another, and overall embraces, with the 5' end of the gone as shown in Table 2, the codens for the following 11 amine acids: (SEQ ID NO: 20)

Phe-Asn-Ala-Met-Ala-Thr-Gly-Asn-Ser-Ala-Arg

Thus, the fusion protein contains in this spacer, inter alia, the amine acids methionine and arginine, which permit cleavage with cyanogen halide or trypsin.

The insert of about 1090 bp is isolated from the plasmid pKK400 (20) by double-digestion with SstI and SphI, and the DNA is ligated into the plasmid pIJ702 (12) which has been opened with the same enzymes. The result is the plasmid pGF1 (21). The ligation mixture is transformed into S. Lividans TK 24, and the plasmid DNA is isolated from thiostreptone-resistant transformants which have tendamistat activity. All positive clones contain the pGF1 SstI-SphI insert which is 1090 bp in size.

Figure 4:
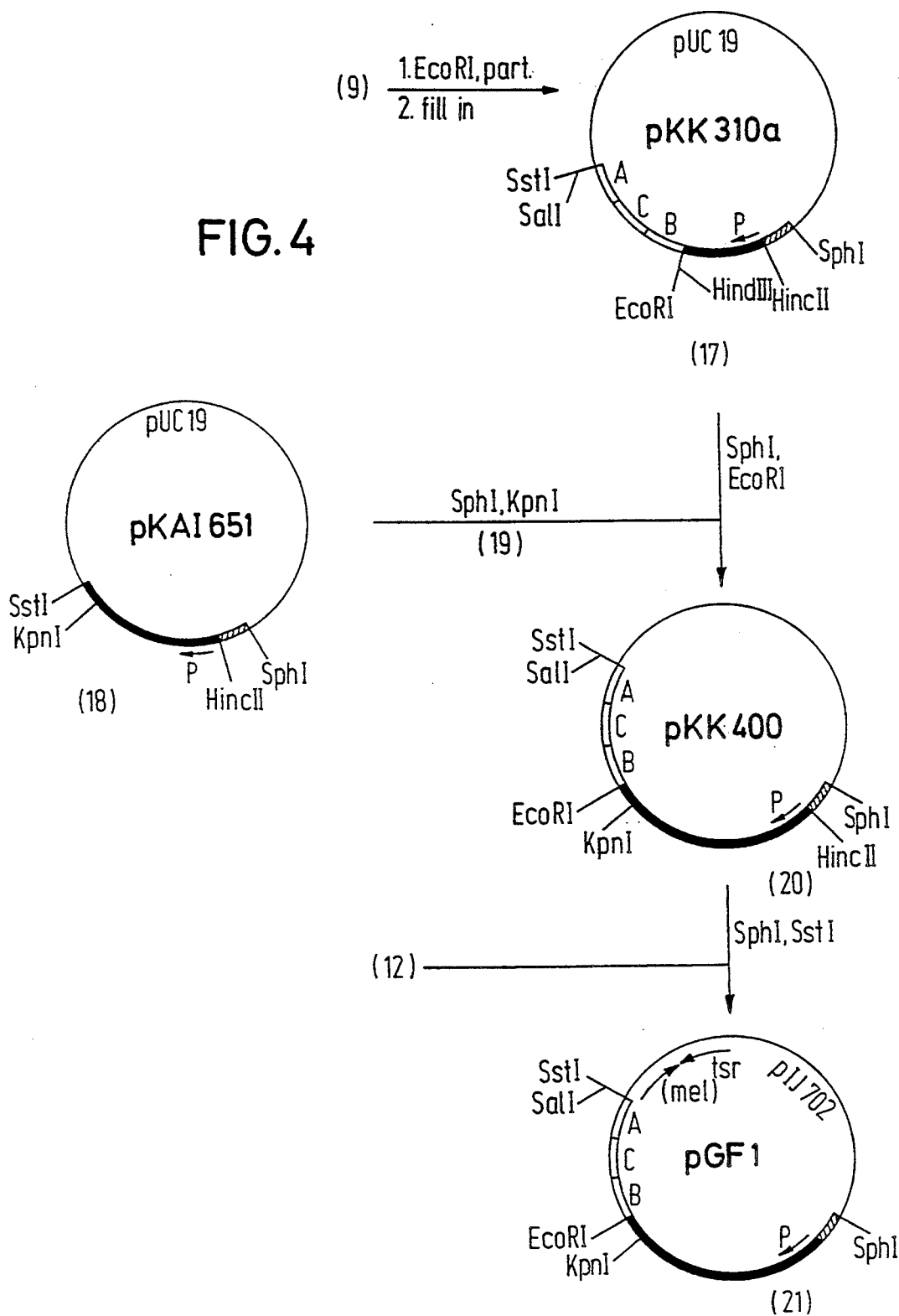
Figure 5:
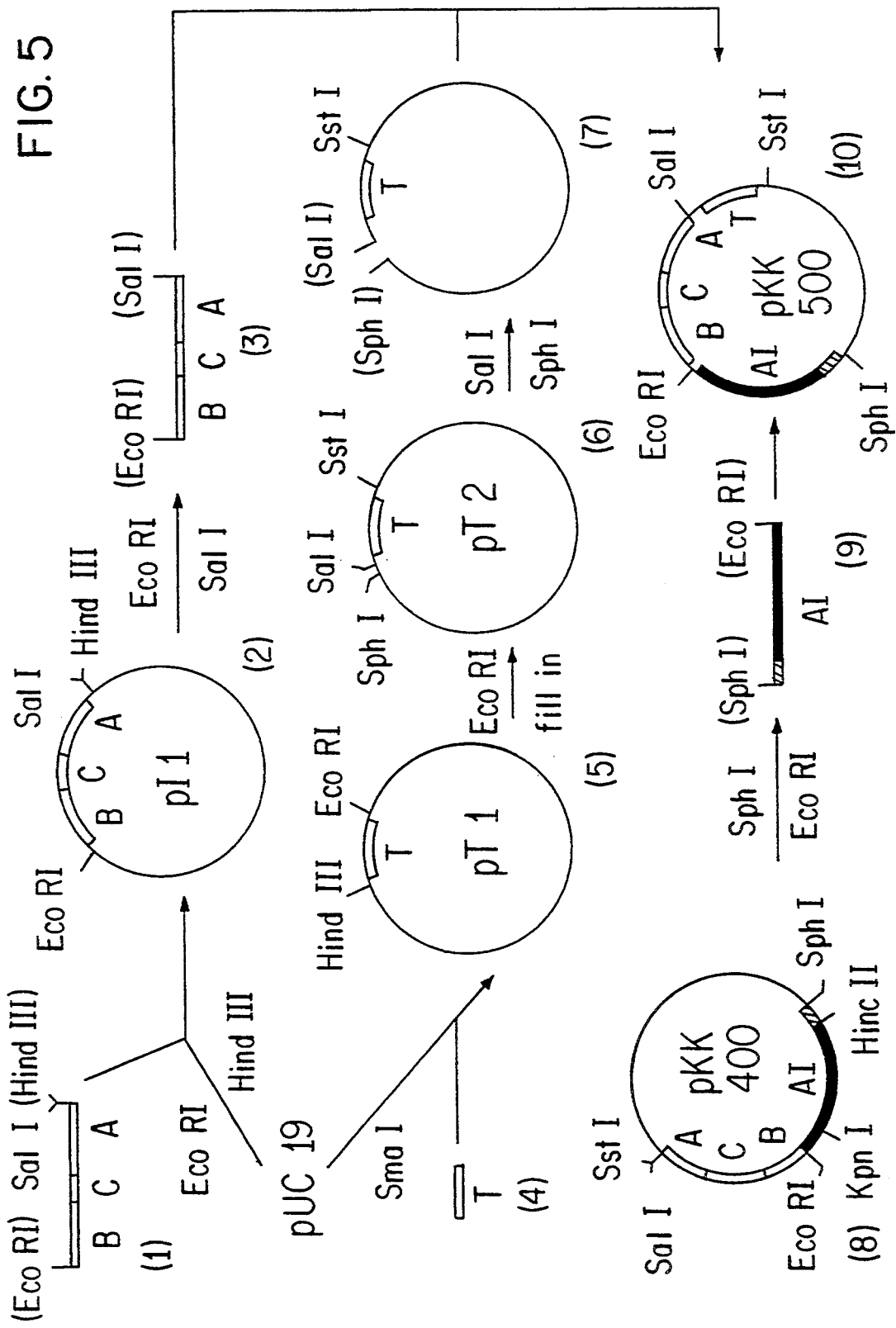

The construction of pGF1 (21) is depicted in FIG. 4.

The tendamistat activity is determined by the plate assay which is described in Example 3 in EP-A1 0,161,629 and in Example 2 in German Offenlegungsschrift 3,536,182.

The fusion protein coded for by pGF1 can be expressed in a known manner. When the transformed strain S. Lividans TK 24 is incubated in shaken flasks at 28° C. for 4 days, and the mycelium is removed from the culture solution by centrifugation, the fusion protein can be detected in the clear solution as follows:

10 to 100 μl of solution are mixed with 20 to 200 μl of 15% strength trichloroacetic acid, and the precipitated protein is concentrated by centrifugation, washed and taken up in SDS-containing sample buffer (U. Laemmli, Nature 227 (1970) 680–685). After incubation at 90° C. for 2 minutes the sample is separated electrophoretically on a 10 to 17% strength SDS polyacrylamide gel. A protein of molecular weight 19 kD is obtained, that is to say in the expected molecular weight range for the fusion protein composed of tendamistat and proinsulin. The fusion protein reacts both with antibodies against tendamistat and with antibodies against insulin.

EXAMPLE 6

The synthetic gene (1) depicted in Table 3 is chemically synthesized in a manner known per se by the phosphoamidite method. In the codon selection account was taken of the preference of Streptomycetes for G and C. As with the gene coding for monkey proinsulin (Table 2) in DE 37 14 866 A1, now issued as German patent P 37 14 866.4, corresponding to EP 0,289,936; also Table 4 of the present application), the gene (1) shown in Table 3 also has at the 5' end a protruding sequence typical for the restriction enzyme EcoRI. The structural gene is followed by two stop codens and a linker sequence with the recognition site for the enzyme SalI. The protruding sequence corresponding to the restriction enzyme HindIII is located at the 3'- end.

The commercially available plasmid pUC19 is cut with the enzymes EcoRI and HindIII, and the synthetic gene (1) shown in Table 3 is ligated in. The result is the plasmid pII (2). After amplification, the synthetic gene is cut out as fragment (3) with the enzymes EcoRI and SalI and employed for the construction described hereinafter.

The plasmid pUC19 is completely digested with SmaI and ligated with the terminator sequence (4) depicted in Table 4. Plasmids which contain this sequence in the correct orientation are called pT1 (5). This plasmid (5) is opened with EcoRI, and the cleavage site is filled in with DNA polymerase (Klenow fragment). The plasmid PT2 (6) is obtained by religation. This plasmid is opened with the enzymes SalI and SphI, and the large fragment (7) is isolated.

The plasmid pKK400 (8) (patent application DE 37 14 866 A1, now issued as German patent P 37 14 866.4, corresponding to EP-A 0,289,936, FIG. 4, (20)) is cut with SphI and EcoRI, and the small fragment (9) with the tendamistat gene is isolated.

Ligation of fragments (3), (7) and (9) results in the plasmid pKK500 (10) in which the tendamistat sequence is followed by the bridging member (SEQ ID NO: 21, aminoacid sequence; SEQ ID NO: 22, nucleic acid sequence):

```
    Phe  Asn  Ala  Met  Ala  Thr  Gly  Asn  Ser  Asn  Gly  Lys
    TTC  AAT  GCG  ATG  GCC  ACC  GGG  ATT  TCG  AAC  GGC  AAG
    AAG  TTA  CGC  TAC  CGG  TGG  CCC  TAA  AGC  TTG  CCG  TTC
                                      EcoRI
``` coding for 12 amino acids, and then by the gene for the proinsulin modified according to the invention. The correct arrangement is checked by cutting with SphI and SstI, resulting in a fragment of 833 bp from the plasmid about 3.5 kb in size. The sequence is confirmed as correct by DNA sequencing using the dideoxy method.

Gene constructions, according to the invention, in which the Lys acting as C peptide is supplemented by another Lys are prepared analogously. For this purpose, the triplet AAG coding for Lys is doubled. The plasmid pI2, and therefrom the vector pKK600, are obtained analogously.

EXAMPLE 7

In analogy to the vector pGF1 (proposed in patent application DE 37 14 866 A1, now issued as German patent P 37 14 866.4, corresponding to EP-A 0,289,936), the expression plasmids pGF2 and pGF3 are prepared from the vectors PKK500 and Pkk600. For this purpose, double digestion with SphI and SstI of each of the vectors pKK500 and pKK600 is carried out to isolate the insert of 823 and 826 bp respectively, and these DNA fragments are ligated into the expression plasmid pIJ702 cleaved with the same enzymes. The ligation mixture is transformed into S. lividans TK 24, and the plasmid DNA is isolated from thiostrepton-resistant transformants which show tendamistat activity (plate test). All the positive clones contain the insert from pKK500 or pKK600 employed.

The expression of the coded fusion protein can be carried out in a known manner. If the transformed strain S. lividans TK 24 is incubated in a shaken flask at 28° C. for four day and the mycelium is separated from the culture solution by centrifugation, the fusion protein can be detected in the clear solution as follows:

20 to 200 µl of 15% strength trichloroacetic acid are added to 10 to 100 µl of solution, and the precipitated protein is concentrated by centrifugation, washed and taken up in SDS-containing sample buffer (U. Laemmli, Nature 227 (1970) 680–685). Incubation at 90° C. for 2 minutes is followed by fractionation by electrophoresis on a 10–17% SDS polyacrylamide gel. A protein of molecular weight 15 kD is obtained, that is to say in the molecular weight range expected for the fusion protein composed of tendamistat and proinsulin. The fusion protein reacts both with antibodies against tendamistat and with antibodies against insulin.

EXAMPLE 8

The expression vector pTF2 (see patent application DE 37 14 866 A1, now issued as German patent P 37 14 866.4 which corresponds to EPA 0,289,936; and Example 4 in the present specification) digested with the restriction enzyme EcoRI and SstI, and the fragment which encodes monkey proinsulin is removed. The fragment 5.65 kbp in size is used for the ligation reaction described below.

These same restriction enzymes are used to cut a DNA fragment which is 285 bp in size and which contains the shortened proinsulin gene, as well as the termination sequence, out of the plasmid pKK500 (Example 6).

Ligation of the fragment 5.65 kbp in size from pTF2 with the fragment 285 bp in size from pKK500 yields the expression plasmid pTF3.

Transformation of protoplasts of Streptomyces lividans TK 24 with the ligation mixture results in clones which are thiostrepton-resistant and secrete a fusion protein which reacts with antibodies against proinsulin. This fusion protein comprises the first 41 amino acids of tendamistat, the bridging member (SEQ ID NO: 23)

Pro-Ser-Leu-Asn-Ser-Asn-Gly-Lys and the shortened proinsulin.

EXAMPLES 9–16

The starting material for the following plasmid constructions is plasmid pKK500 which was proposed in EP-A 0,367,163. This plasmid differs from plasmid PKK400 known from EP-A 0,289,936 in that the proinsulin gene is replaced by an analogous gene which, instead of the C chain, merely encodes the amino acid lysine, and in that a terminator sequence is inserted immediately downstream of this "mini-proinsulin" gene. Tables 1 and 2 from EP-A 0,367,163, in which the "mini-proinsulin" gene and the terminator sequence, respectively, are shown, are enclosed as Tables 3 and 4 in the annex to the description.

The plasmids pKK400 and pKK500 contain a XmaIII cleavage site in the signal sequence of the α-amylase inhibitor gene (in the region of triplets −5 to −7).

EXAMPLE 9

Plasmid pKK500 is opened up with the restriction enzymes EcoRI and XmaIII, and the large fragment is separated by gel electrophoresis on a 0.8% agarose gel and isolated by electroelution. This fragment is ligated with the DNA fragment (1) (SEQ ID NO: 24, amino acid sequence; SEQ ID NOS: 25 and 26, nucleic acid sequence):

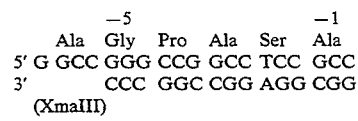

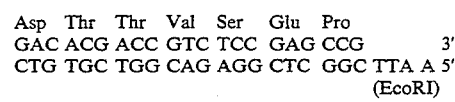

which has been synthesized by the phosphoramidite method, and the ligation mixture is transformed into E. coli. Plasmid pKK510 is obtained. This plasmid encodes a preproinsulin in which the signal sequence of tendamistat is followed by the first 7 amino acids of tendamistat which are followed by the mini-proinsulin chain.

EXAMPLE 10

In analogy with the process described in Example 5, as well as EP-A 0,289,936 for transferring plasmid pKK400 into expression plasmid pGF1, plasmid pKK510 is transferred into expression plasmid pKF1:

The isolated plasmid DNA of pKK510 is cut with the restriction enzymes SphI and SstI, and the small fragment with the fusion gene is isolated. The commercial expression plasmid pIJ 702 (obtainable from John Innes Foundation, Norwich, England) is cut with the same enzymes and the large fragment is isolated. These two isolated fragments are ligated, the ligation mixture transformed into S. lividans TK24 and the plasmid is isolated from the thiostrepton-resistant white (i.e. not capable of forming melanin) transformants. Clones which carry the introduced insert are tested for the formation of fusion proteins in a shake culture.

The encoded fusion protein is expressed in a manner known per se: if the transformed strain is incubated in a shaken flask at above 25° C. for 4 days and the mycelium is separated from the culture solution by centrifugation, it is possible, after electrophoresis of 20 µl of culture filtrate in a 15% polyacrylamide gel, to visualize by dyeing with COOMASSIE Blue the fusion protein formed in the culture supernatant as an additional protein band which does not occur in a control experiment in which the strain was transformed only with pIJ 702.

If the culture filtrate is treated with lysyl endoproteinase, it is possible to detect de-(B30)-Thr-insulin, which is verified by an authentic control on gel electrophoresis.

Furthermore, it is possible to detect the fusion protein in the culture filtrate with insulin antibodies either in an immunoblot or with an insulin RIA.

EXAMPLE 11

The procedure according to Examples 9 and 10 is carried out, but the synthetic fragment (2) (SEQ ID NO: 27, amino acid sequence; SEQ ID NOS: 28 and 29, nucleic acid sequence):

```
             -5                    -1
        Ala Gly Pro Ala Ser Ala
5' G    GCC GGG CCG GCC TCC GCC
3'      CCC GGC CGG AGG CGG
    (XmaIII)

5
        Asp Thr Thr Val Ser Glu Pro Asp Pro
        GAC ACG ACC GTC TCC GAG CCC GAC CCG         3'
        CTG TGC TGG CAG AGG CTC GGG CTG GGC TTA A   5'
                                              (EcoRI)
``` is used and the plasmids pKK320 and pKF2, respectively, are obtained in this way.

These plasmids encode a fusion protein which differs from the one according to Examples 9 and 10 in that the first 7 amino acids of tendamistat are followed by aspartic acid (instead of the natural amino acid alanine) and that this is followed by the ninth amino acid in tendamistat, proline. By exchanging alanine for aspartic acid, an additional positive charge is therefore introduced into the ballast portion of the fusion protein. Surprisingly, yields about 20 to 30% higher than in Example 10 are obtained.

EXAMPLE 12

If the procedure according to Examples 9 and 10 is carried out, but the synthetic fragment (3) (SEQ ID NO: 30, amino acid sequence; SEQ ID NOS: 31 and 32, nucleic acid sequence):

```
             -5                    -1
        Ala Gly Pro Ala Ser Ala
5' G    GCC GGG CCG GCC TCC GCC
3'      CCC GGC CGG AGG CGG
    (XmaIII)

5
        Asp Thr Thr Val Ser Glu Pro Ala Pro
        GAC ACG ACC GTC TCC GAG CCC GCA CCG         3'
        CTG TGC TGG CAG AGG CTC GGG CGT GGC TTA A   5'
``` is used, the plasmids pKK330 and pKF3, respectively, are obtained in this way. These plasmids differ from those according to Examples 9 and 10 in that they encode the first 9 natural amino acids of tendamistat. In comparison with Example 10, yields about 10% higher are obtained.

EXAMPLE 13

The fusion protein encoded by pKK500 contains between the tendamistat portion and the B chain of proinsulin a linker sequence which codes for the amino acids Asn-Ser-Asn-Gly-Lys. (SEQ ID NO. 33) This terminal Lys and the Lys representing the C chain are replaced by Arg as described below. In this procedure, the single StyI cleavage site in the region of codons B30 to A1 in the proinsulin sequence is used.

Isolated plasmid DNA from pKK500 is cut using StyI, digested with S1 nuclease to remove protruding ends and the excess nuclease is extracted using phenol-chloroform. The linearized plasmid is then subsequently cut with EcoRI, and the large fragment is electrophoretically separated off and isolated by electroelution. This fragment is ligated with the synthetic fragment (4) (SEQ ID NO: 34, amino acid sequence; SEQ ID NO: 35, nucleic acid sequence):

```
                                            B1                                10
        Asn     Ser     Asn     Gly     Arg     Phe     Val     Asn     Gln     His     Leu     Cyn     Gly     Ser     His
        AAT     TCG     AAC     GGC     CGC     TTC     GTC     AAC     CAG     CAC     CTG     TGC     GGC     TCG     CAC
                GC      TTG     CCG     GCG     AAG     CAG     TTG     GTC     GTG     GAC     ACG     CCG     AGC     GTG
    (EcoRI)

20                                                                              30
        Leu     Val     Glu     Ala     Leu     Tyr     Leu     Val     Cyn     Gly     Glu     Arg     Gly     Phe     Phe
        CTC     GTG     GAG     GCC     CTC     TAC     CTG     GTG     TGC     GGG     GAG     CGC     GGC     TTC     TTC
        GAG     CAC     CTC     CGG     GAG     ATG     GAC     CAC     ACG     CCC     CTC     GCG     CCG     AAG     AAG

B30     C(B31)
        Tyr     Thr     Pro     Lys     Thr     Arg
        TAC     ACC     CCC     AAG     ACC     CGC
        ATG     TGG     GGG     TTC     TGG     GCG
``` and the ligation mixture is transformed into *E. coli*. The desired clones are tested by restriction analysis of the plasmid contained, using the newly developed SstII cleavage site. Furthermore, the entire SPhI-SsTI fragment is sequenced.

In order to express the encoded fusion protein, the fragment, which has been checked by sequence analysis, is ligated into the vector pIJ 702, which has been cut with the same enzymes, resulting in the expression vector pGF4.

The secreted fusion protein encoded by pGF4 can be detected, on the one hand, by the e-amylase inhibitor plate test (EP A 0,161,629, Example 3) and, on the other hand, from the supernatant of the shake culture in analogy with Example 10.

EXAMPLE 14

If fragment (4) is, in analogy with Example 13, inserted into the vectors pKK510, 520 and 530, the vector pKK610, 620 and 630 are obtained. The incorporation of the respective SphI-SstI fragments with the coding sequence for the fusion proteins into the vector pIJ 702 results in the expression vectors pKF11, 12 and 13. The expression of the secreted fusion proteins is tested in analogy with Example 10.

EXAMPLE 15

In order to increase the expression of derivatives of the plasmid pIJ 702, the melanin promoter is deleted therefrom by digestion with PstI and SphI and is replaced by the synthetic fragment (5) (SEQ ID NO: 36): this purpose, a modification of the amino acids upstream of amino acid B1 (Phe) is suitable:

```
PstI  BclI
      10        20        30        40        50
CT GCA GT GAT CAG GGG GAC CCT T GT GCG AAT TT CCG TT ACG GGT TT GGG T GGT AGG G
GA CGT CAC TAG TCC CCC T GGG AAC ACG CTT AAA GGC AAT GCC CAA ACC CAC CAT CCC

SphI
  60        70        80
ACG CAC CCG AAG AGG AGG CCC CAG CAT GC
TGC GTG GGC TT CT CCT CCG GGG T CGT ACG
```

A tandem construction of the synthetic and the tendamistat promoter is thereby obtained. The plasmid is called pGR110.

If the synthetic fragments (1), (2) and (3) are, after cutting with SphI and SstI, inserted into pGR110, the expression vectors pGR200, 210 and 220 result. In an analogous way, the expression vectors pGR250, 260 and 270 are obtained with fragment (4).

EXAMPLE 16

If it is intended to produce human insulin from the insulin precursors by combining trypsin, or an enzyme with an identical effect, and carboxypeptidase B, it is advantageous to cleave off rapidly the ballast portion in the course of the cleavage reaction in order to favor the cleavage reaction leading to the B31 (Arg)-insulin. For The procedure is analogous to Example 9 and the plasmid pKK500 is opened using the restriction enzymes EcoRI and DraIII. The original fragment is then replaced by DNA fragment (6) (SEQ ID NO: 37, amino acid sequence; SEQ ID NO: 38, nucleic acid sequence):

```
                    B1
     Asn Ser Ala Arg Phe Val Asn Gln His Leu Cys Gly Ser His Leu
5' AAT TCG GCC CGC TTC GTC AAC CAG CAC CTG TGC GGC TCG CAC CTC 3'
3'     GC CGG GCG AAG CAG TTG GTC GTG GAC ACG CCG AGC GTG      5'
   (EcoRI)                                              (DraIII)
``` which has been synthesized by the phosphoramidite method. Cloning into *E. coli* and expression in *Streptomyces lividans* are carried out in accordance with Example 9 and Example 10, respectively. Plasmid pKK640 and expression plasmid pKF14 result. The plasmid which results according to Example 13 (after incorporation of fragment (4)) can be treated in an analogous way. The plasmids pKK650 and pKF15 are obtained in this way.

TABLE 1

| ANNEX |
|---|
| DNA sequence (coding strand) and amino acid sequence of tendamistat |

| | | | | 5 | | | | | | 10 | | |
|---|---|---|---|---|---|---|---|---|---|---|---|---|
| 5'-GAC | ACG | ACC | GTC | TCC | GAG | CCC | GCA | CCC | TCC | TGC | GTG |
| NH2-Asp | Thr | Thr | Val | Ser | Glu | Pro | Ala | Pro | Ser | Cys | Val |
| | | 15 | | | | 20 | | | | | |
| ACG | CTC | TAC | CAG | AGC | TGG | CGG | TAC | TCA | CAG | GCC | GAC |
| Thr | Leu | Tyr | Gln | Ser | Trp | Arg | Tyr | Ser | Gln | Ala | Asp |
| 25 | | | | | 30 | | | | | 35 | |
| AAC | GGC | TGT | GCC | GAG | ACG | GTG | ACC | GTG | AAG | GTC | GTC |
| Asn | Gly | Cys | Ala | Glu | Thr | Val | Thr | Val | Lys | Val | Val |
| | | | 40 | | | | | 45 | | | |
| TAC | GAG | GAC | GAC | ACC | GAA | GGC | CTG | TGC | TAC | GCC | GTC |
| Tyr | Glu | Asp | Asp | Thr | Glu | Gly | Leu | Cys | Tyr | Ala | Val |
| | 50 | | | | | 55 | | | | | 60 |
| GCA | CCG | GGC | CAG | ATC | ACC | ACC | GTC | GGC | GAC | GGC | TAC |
| Ala | Pro | Gly | Gln | Ile | Thr | Thr | Val | Gly | Asp | Gly | Tyr |
| | | | | 65 | | | | | | 70 | |
| ATC | GGC | TCG | CAC | GGC | CAC | GCG | CGC | TAC | CTG | GCT | CGC |
| Ile | Gly | Ser | His | Gly | His | Ala | Arg | Tyr | Leu | Ala | Arg |
| TGC | CTT | TAG-3' | | | | | | | | | |
| Cys | Leu | Stp | | | | | | | | | |

TABLE 2

(SEQ ID NOS: 41 and 42, nucleic acid sequence; SEQ ID NO: 43, amino acid sequence):

```
                              5'      AAT     TCT     GCA     AGA
                              3'              GA      CGT     TCT
                                           (Asn)Ser   Ala     Arg
                                             (EcoRI)
B 1
```

TABLE 2-continued

| | | | | | | | | | | | | | | |
|---|---|---|---|---|---|---|---|---|---|---|---|---|---|---|
| TTT | GTG | AAC | CAG | CAC | CTG | TGC | GGC | TCC | CAC | CTA | GTG | GAA | GCT | CTC |
| AAA | CAC | TTG | GTC | GTG | GAC | ACG | CCG | AGG | GTG | GAT | CAC | CTT | CGA | GAG |
| Phe | Val | Asn | Gln | His | Leu | Cys | Gly | Ser | His | Leu | Val | Glu | Ala | Leu |
| TAC | CTG | GTG | TGC | GGG | GAG | CGA | GGC | TTC | TTC | TAC | ACA | CCC | AAG | ACC |
| ATG | GAC | CAC | ACG | CCC | CTC | GCT | CCG | AAG | AAG | ATG | TGT | GGG | TTC | TGG |
| Tyr | Leu | Val | Cys | Gly | Glu | Arg | Gly | Phe | Phe | Tyr | Thr | Pro | Lys | Thr |

C 1

| | | | | | | | | | | | | | | |
|---|---|---|---|---|---|---|---|---|---|---|---|---|---|---|
| CGC | CGG | GAG | GCA | GAG | GAC | CCT | CAG | GTG | GGG | CAG | GTG | GAG | CTG | GGC |
| GCG | GCC | CTC | CGT | CTC | CTG | GGA | GTC | CAC | CCC | GTC | CAC | CTC | GAC | CCG |
| Arg | Arg | Glu | Ala | Glu | Asp | Pro | Gln | Val | Gly | Gln | Val | Glu | Leu | Gly |
| GGG | GGC | CCT | GGC | GCA | GGC | AGC | CTG | CAG | CCC | TTG | GCG | CTG | GAG | GGG |
| CCC | CCG | GGA | CCG | CGT | CCG | TCG | GAC | GTC | GGG | AAC | CGC | GAC | CTC | CCC |
| Gly | Gly | Pro | Gly | Ala | Gly | Ser | Leu | Gln | Pro | Leu | Ala | Leu | Glu | Gly |

A 1

| | | | | | | | | | | | | | | |
|---|---|---|---|---|---|---|---|---|---|---|---|---|---|---|
| TCC | CTG | CAG | AAG | CGC | GGC | ATC | GTG | GAG | CAG | TGC | TGC | ACC | AGC | ATC |
| AGG | GAC | GTC | TTC | GCG | CCG | TAG | CAC | CTC | GTC | ACG | ACG | TGG | TCG | TAG |
| Ser | Leu | Gln | Lys | Arg | Gly | Ile | Val | Glu | Gln | Cys | Cys | Thr | Ser | Ile |
| TGC | TCC | CTC | TAC | CAG | CTG | GAG | AAC | TAC | TGC | AAC | TAA | TAG | TCG | ACC |
| ACG | AGG | GAG | ATG | GTC | GAC | CTC | TTG | ATG | ACG | TTG | ATT | ATC | AGC | TGG |
| Cys | Ser | Leu | Tyr | Gln | Leu | Glu | Asn | Tyr | Cys | Asn | | | | SalI |

| | | | | |
|---|---|---|---|---|
| TGC | AGC | CA | | 3' |
| ACG | TCG | GTT | CGA | 5' |
| PstI | | (HindIII) | | |

TABLE 3

(SEQ ID NO: 44, amino acid sequence; SEQ ID NOS: 45 and 46, nucleic acid sequence):

| | | | | | B¹ | | | | 10 | | | | | |
|---|---|---|---|---|---|---|---|---|---|---|---|---|---|---|
| ASN | SER | ASN | GLY | LYS | PHE | VAL | ASN | GLN | HIS | LEU | CYS | GLY | SER | HIS |
| AAT | TCG | AAC | GGC | AAG | TTC | GTC | AAC | CAG | CAC | CTG | TGC | GGC | TCG | CAC |
| (EcoRI) | GC | TTG | CCG | TTC | AAG | CAG | TTG | GTC | GTG | GAC | ACG | CCG | AGC | GTG |

| | | | | 20 | | | | | | | | | | 30 |
|---|---|---|---|---|---|---|---|---|---|---|---|---|---|---|
| LEU | VAL | GLU | ALA | LEU | TYR | LEU | VAL | CYS | GLY | GLU | ARG | GLY | PHE | PHE |
| CTC | GTG | GAG | GCC | CTC | TAC | CTG | GTG | TGC | GGG | GAG | CGC | GGC | TTC | TTC |
| GAG | CAC | CTC | CGG | GAG | ATG | GAC | CAC | ACG | CCC | CTC | GCG | CCG | AAG | AAG |

| | | | | C | A¹ | | | 40 | | | | | | |
|---|---|---|---|---|---|---|---|---|---|---|---|---|---|---|
| TYR | THR | PRO | LYS | THR | LYS | GLY | ILE | VAL | GLU | GLN | CYS | CYS | THR | SER |
| TAC | ACC | CCC | AAG | ACC | AAG | GGC | ATC | GTG | GAG | CAG | TGC | TGT | ACG | TCC |
| ATG | TGG | GGG | TTC | TGG | TTC | CCG | TAG | CAC | CTC | GTC | ACG | ACA | TGC | AGG |

| | | | 50 | | | | | | | | | |
|---|---|---|---|---|---|---|---|---|---|---|---|---|
| ILE | CYS | SER | LEU | TYR | GLN | LEU | GLU | ASN | TYR | CYS | ASN | STP | STP |
| ATC | TGC | TCC | CTC | TAC | CAG | CTC | GAG | AAC | TAC | TGC | AAC | TAG | TAA |
| TAG | ACG | AGG | GAG | ATG | GTC | GAG | CTC | TTG | ATG | ACG | TTG | ATC | ATT |

| | | | | | |
|---|---|---|---|---|---|
| GTC | GAC | CTG | CAG | CCA | |
| CAG | CTG | GAC | GTC | GGT | TCG | A |
| SalI | | | | (HindIII) | |

TABLE 4

(SEQ ID NO: 47):

5'-CGATAAACCGATACAATTAAAGGCTCCTTTTGGAGCCTTTTTTTTGGAGATTTTCAACGTGGATC
GCTATTTGGCTATGTTAATTTCCGAGGAAAACCTCGGAAAAAAAAACCTCTAAAAGTTGCACCTAG-5'

What is claimed is:

1. A fusion protein which comprises a tendamistat portion, other than the signal peptide of tendamistat, and a desired protein, wherein the first seven to ten amino acids of the N-terminal portion of tendamistat are coupled to the desired protein.

2. A fusion protein as claimed in claim 1, wherein the first seven to ten amino acids of the N-terminal portion of tendamistat are coupled via a bridge sequence to the desired protein.

3. A process for making a desired protein, which comprises cleaving a fusion protein as defined in claim 2.

4. A process for preparing a fusion protein of claim 1, which comprises ligating a structural gene for a desired protein onto the 3' end of the coding strand of a DNA encoding the first seven to ten amino acids of the N-terminal portion of tendamistat, expressing the ligated gene and DNA in a Streptomycetes host cell, and isolating secreted fusion protein from the supernatant.

5. A process as claimed in claim 4, wherein the DNA encoding the first seven to ten amino acids of the N-terminal portion of tendamistat is ligated to the gene for the desired protein via a DNA encoding a bridge sequence.

6. A process as claimed in claim 5, wherein the desired protein is a proinsulin derivative in which the B chain is connected to the A chain via a bridge sequence comprising Lys or Lys-Lys.

7. A process as claimed in claim 4, wherein the desired protein is a proinsulin derivative in which the B chain is connected to the A chain via a bridge sequence comprising Lys or Lys-Lys.

8. A substantially purified DNA which encodes the fusion protein as claimed in claim 1.

9. A vector containing a substantially purified DNA as claimed in claim 8.

10. A Streptomycetes cell containing a vector as claimed in claim 9.

11. A fusion protein as claimed in claim 1, wherein the desired protein is a proinsulin derivative in which the B chain of the proinsulin derivative is connected to the A chain of the proinsulin derivative via a bridge sequence comprising Lys or Lys-Lys.

12. A fusion protein as claimed in claim 11, wherein the first seven to ten amino acids of the N-terminal portion of tendamistat are ligated to the proinsulin derivative via a bridge sequence.

13. A substantially purified DNA which encodes the fusion protein as claimed in claim 11.

14. A vector containing a substantially purified DNA as claimed in claim 13.

15. A Streptomycetes cell containing a vector as claimed in claim 14.

16. A process for preparation of a desired protein, which comprises cleaving the fusion protein as claimed in claim 1 to separate the tendamistat portion from the desired portion of said fusion protein.

17. A process for the production of a fusion protein, which comprises ligating the structural gene for a desired protein to a DNA coding for the signal sequence and the first seven to ten amino-terminal amino acids of tendamistat, expressing this DNA sequence in a Streptomycetes host cell and isolating the secreted fusion protein from the supernatant.

18. A substantially purified DNA encoding a signal sequence, the first seven to ten amino acids of the N-terminal portion of tendamistat, and another protein.

19. A substantially purified DNA encoding a signal sequence, the first eight to ten amino acids of the N-terminal portion of tendamistat, and another protein, wherein the eighth amino acid of the N-terminal portion of tendamistat has been replaced by aspartic acid.

20. The fusion protein of claim 1, wherein said first seven to ten amino acids of the N-terminal portion of tendamistat consists of the first seven amino acids of the N-terminal portion of tendamistat.

21. The fusion protein of claim 1, wherein said first seven to ten amino acids of the N-terminal portion of tendamistat consists of the first nine amino acids of the N-terminal portion of tendamistat, and wherein the eighth amino acid of the N-terminal portion of tendamistat has been replaced by aspartic acid.

22. The fusion protein of claim 1, wherein said first seven to ten amino acids of the N-terminal portion of tendamistat consists of the first nine amino acids of the N-terminal portion of tendamistat.

23. The process of claim 17, wherein said first seven to ten amino-terminal amino acids of tendamistat consists of the first seven amino-terminal amino acids of tendamistat.

24. The process of claim 17, wherein said first seven to ten amino-terminal amino acids of tendamistat consists of the first nine amino-terminal amino acids of tendamistat, and wherein the eighth amino-terminal amino acid of tendamistat has been replaced by aspartic acid.

25. The process of claim 17, wherein said first seven to ten amino-terminal amino acids of tendamistat consists of the first nine amino-terminal amino acids of tendamistat.

26. The substantially purified DNA of claim 18, wherein said first seven to ten amino acids of the N-terminal portion of tendamistat consists of the first seven amino acids of the N-terminal portion of tendamistat.

27. The substantially purified DNA of claim 18, wherein said first seven to ten amino acids of the N-terminal portion of tendamistat consists of the first nine amino acids of the N-terminal portion of tendamistat.

* * * * *

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:

( A ) LENGTH: 5 amino acids
                ( B ) TYPE: amino acid
                ( D ) TOPOLOGY: linear ( i i ) MOLECULE TYPE: peptide ( x i ) SEQUENCE DESCRIPTION: SEQ ID NO:1:

Ala  Ser  Met  Thr  Arg
    1                      5

( 2 ) INFORMATION FOR SEQ ID NO:2:

( i ) SEQUENCE CHARACTERISTICS:
                ( A ) LENGTH: 4 amino acids
                ( B ) TYPE: amino acid
                ( D ) TOPOLOGY: unknown ( i i ) MOLECULE TYPE: peptide ( x i ) SEQUENCE DESCRIPTION: SEQ ID NO:2:

Ile  Glu  Gly  Arg
    1

( 2 ) INFORMATION FOR SEQ ID NO:3:

( i ) SEQUENCE CHARACTERISTICS:
                ( A ) LENGTH: 12 base pairs
                ( B ) TYPE: nucleic acid
                ( C ) STRANDEDNESS: double
                ( D ) TOPOLOGY: linear ( i i ) MOLECULE TYPE: Other
                ( A ) DESCRIPTION: synthetic DNA ( x i ) SEQUENCE DESCRIPTION: SEQ ID NO:3:

CCCAAGCTTG GG                                                                                        12

( 2 ) INFORMATION FOR SEQ ID NO:4:

( i ) SEQUENCE CHARACTERISTICS:
                ( A ) LENGTH: 7 amino acids
                ( B ) TYPE: amino acid
                ( D ) TOPOLOGY: unknown ( i i ) MOLECULE TYPE: peptide ( x i ) SEQUENCE DESCRIPTION: SEQ ID NO:4:

Glu  Gly  Pro  Ser  Leu  Gly  Leu
    1                      5

( 2 ) INFORMATION FOR SEQ ID NO:5:

( i ) SEQUENCE CHARACTERISTICS:
                ( A ) LENGTH: 21 base pairs
                ( B ) TYPE: nucleic acid
                ( C ) STRANDEDNESS: double
                ( D ) TOPOLOGY: linear ( x i ) SEQUENCE DESCRIPTION: SEQ ID NO:5:

GAAGGCCCAA GCTTGGGCCT G                                                                              21

( 2 ) INFORMATION FOR SEQ ID NO:6:

( i ) SEQUENCE CHARACTERISTICS:
                ( A ) LENGTH: 12 base pairs
                ( B ) TYPE: nucleic acid
                ( C ) STRANDEDNESS: both
                ( D ) TOPOLOGY: linear ( i i ) MOLECULE TYPE: Other
                ( A ) DESCRIPTION: synthetic DNA ( x i ) SEQUENCE DESCRIPTION: SEQ ID NO:6:

AGCTTGATGG CG                                                                                    1 2

( 2 ) INFORMATION FOR SEQ ID NO:7:

( i ) SEQUENCE CHARACTERISTICS:
    ( A ) LENGTH: 12 base pairs
    ( B ) TYPE: nucleic acid
    ( C ) STRANDEDNESS: both
    ( D ) TOPOLOGY: linear ( i i ) MOLECULE TYPE: Other
    ( A ) DESCRIPTION: synthetic DNA ( i v ) ANTI-SENSE: YES ( i x ) FEATURE:
    ( A ) NAME/KEY: misc_feature
    ( B ) LOCATION: 5..12
    ( D ) OTHER INFORMATION: /note="Sequence ID No. 7 is
          complementary to Sequence ID No. 6 from positions
          5-12 of Sequence ID No. 6."

( x i ) SEQUENCE DESCRIPTION: SEQ ID NO:7:

AATTCGCCAT CA                                                                                    1 2

( 2 ) INFORMATION FOR SEQ ID NO:8:

( i ) SEQUENCE CHARACTERISTICS:
    ( A ) LENGTH: 9 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:8:

Gly  Pro  Ser  Leu  Met  Ala  Asn  Ser  Phe
   1                   5

( 2 ) INFORMATION FOR SEQ ID NO:9:

( i ) SEQUENCE CHARACTERISTICS:
    ( A ) LENGTH: 27 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:9:

GGCCCAAGCT TGATGGCGAA TTCTTTT                                                                    2 7

( 2 ) INFORMATION FOR SEQ ID NO:10:

( i ) SEQUENCE CHARACTERISTICS:
    ( A ) LENGTH: 12 base pairs
    ( B ) TYPE: nucleic acid
    ( C ) STRANDEDNESS: both
    ( D ) TOPOLOGY: linear ( x i ) SEQUENCE DESCRIPTION: SEQ ID NO:10:

AATTCAAGCT TG                                                                                    1 2

( 2 ) INFORMATION FOR SEQ ID NO:11:

( i ) SEQUENCE CHARACTERISTICS:
    ( A ) LENGTH: 12 base pairs
    ( B ) TYPE: nucleic acid
    ( C ) STRANDEDNESS: both
    ( D ) TOPOLOGY: linear ( i x ) FEATURE:
    ( A ) NAME/KEY: misc_feature
    ( B ) LOCATION: 5..12

(D) OTHER INFORMATION: /note="Sequence ID No. 11 is
complementary to Sequence ID No. 10 from positions
5-12 of Sequence ID No. 10."

(x i) SEQUENCE DESCRIPTION: SEQ ID NO:11:

AATTCAAGCT TG     12

(2) INFORMATION FOR SEQ ID NO:12:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (x i) SEQUENCE DESCRIPTION: SEQ ID NO:12:

Gly Pro Ser Leu Asn Phe Ala Arg
1               5

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (x i) SEQUENCE DESCRIPTION: SEQ ID NO:13:

GGCCCAAGCT TGAATTCTGC AAGATTT     27

(2) INFORMATION FOR SEQ ID NO:14:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:14:

CGAGGTACCG GGCGT     15

(2) INFORMATION FOR SEQ ID NO:15:

(i) SEQUENCE CHARACTERISTICS:
        (A) LENGTH: 5 amino acids
        (B) TYPE: amino acid
        (D) TOPOLOGY: unknown (ii) MOLECULE TYPE: peptide (x i) SEQUENCE DESCRIPTION: SEQ ID NO:15:

His Ala Arg Tyr Leu
1               5

(2) INFORMATION FOR SEQ ID NO:16:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (x i) SEQUENCE DESCRIPTION: SEQ ID NO:16:

CACGCCCGCT ACCTC     15

(2) INFORMATION FOR SEQ ID NO:17:

(i) SEQUENCE CHARACTERISTICS:
        (A) LENGTH: 13 amino acids ( B ) TYPE: amino acid
( D ) TOPOLOGY: unknown ( i i ) MOLECULE TYPE: peptide ( x i ) SEQUENCE DESCRIPTION: SEQ ID NO:17:

Tyr Leu Ala Arg Cys Leu Phe Asn Ala Met Ala Thr Gly
1               5                   10

( 2 ) INFORMATION FOR SEQ ID NO:18:

( i ) SEQUENCE CHARACTERISTICS:
( A ) LENGTH: 36 base pairs
( B ) TYPE: nucleic acid
( C ) STRANDEDNESS: both
( D ) TOPOLOGY: linear ( x i ) SEQUENCE DESCRIPTION: SEQ ID NO:18:

CTCGCTCGCT GCCTTTTCAA TGCGATGGCC ACCGGG                     36

( 2 ) INFORMATION FOR SEQ ID NO:19:

( i ) SEQUENCE CHARACTERISTICS:
( A ) LENGTH: 44 base pairs
( B ) TYPE: nucleic acid
( C ) STRANDEDNESS: both
( D ) TOPOLOGY: linear ( i v ) ANTI-SENSE: YES ( i x ) FEATURE:
( A ) NAME/KEY: misc_feature
( B ) LOCATION: 5..40
( D ) OTHER INFORMATION: /note="Sequence ID No. 19 is
complementary to Sequence ID No. 18 at positions
1-36 of Sequence ID No. 18."

( x i ) SEQUENCE DESCRIPTION: SEQ ID NO:19:

AATTCCCGGT GGCCATCGCA TTGAAAAGGC AGCGAGCGAG GTAC            44

( 2 ) INFORMATION FOR SEQ ID NO:20:

( i ) SEQUENCE CHARACTERISTICS:
( A ) LENGTH: 11 amino acids
( B ) TYPE: amino acid
( D ) TOPOLOGY: unknown ( i i ) MOLECULE TYPE: peptide ( x i ) SEQUENCE DESCRIPTION: SEQ ID NO:20:

Phe Asn Ala Met Ala Thr Gly Asn Ser Ala Arg
1               5                   10

( 2 ) INFORMATION FOR SEQ ID NO:21:

( i ) SEQUENCE CHARACTERISTICS:
( A ) LENGTH: 12 amino acids
( B ) TYPE: amino acid
( D ) TOPOLOGY: unknown ( i i ) MOLECULE TYPE: peptide ( x i ) SEQUENCE DESCRIPTION: SEQ ID NO:21:

Phe Asn Ala Met Ala Thr Gly Asn Ser Asn Gly Lys
1               5                   10

( 2 ) INFORMATION FOR SEQ ID NO:22:

( i ) SEQUENCE CHARACTERISTICS:
( A ) LENGTH: 36 base pairs
( B ) TYPE: nucleic acid
( C ) STRANDEDNESS: double (D) TOPOLOGY: linear (xi) SEQUENCE DESCRIPTION: SEQ ID NO:22:

TTCAATGCGA TGGCCACCGG GATTTCGAAC GGCAAG    36

(2) INFORMATION FOR SEQ ID NO:23:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (xi) SEQUENCE DESCRIPTION: SEQ ID NO:23:

Pro Ser Leu Asn Ser Asn Gly Lys
1               5

(2) INFORMATION FOR SEQ ID NO:24:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (xi) SEQUENCE DESCRIPTION: SEQ ID NO:24:

Ala Gly Pro Ala Ser Ala Asp Thr Thr Val Ser Glu Pro
-5              -1                   5

(2) INFORMATION FOR SEQ ID NO:25:

(i) SEQUENCE CHARACTERISTICS:
        (A) LENGTH: 40 base pairs
        (B) TYPE: nucleic acid
        (C) STRANDEDNESS: both
        (D) TOPOLOGY: linear (ii) MOLECULE TYPE: Other nucleic acid
        (A) DESCRIPTION: synthetic DNA (xi) SEQUENCE DESCRIPTION: SEQ ID NO:25:

GGCCGGGCCG GCCTCCGCCG ACACGACCGT CTCCGAGCCG    40

(2) INFORMATION FOR SEQ ID NO:26:

(i) SEQUENCE CHARACTERISTICS:
        (A) LENGTH: 40 base pairs
        (B) TYPE: nucleic acid
        (C) STRANDEDNESS: both
        (D) TOPOLOGY: linear (ii) MOLECULE TYPE: Other nucleic acid
        (A) DESCRIPTION: synthetic DNA (iv) ANTI-SENSE: YES (ix) FEATURE:
        (A) NAME/KEY: misc_feature
        (B) LOCATION: 5..40
        (D) OTHER INFORMATION: /note="Sequence ID No. 26 is
        complementary to Sequence ID No. 25 at positions
        5-36 of Sequence ID No. 25."

(xi) SEQUENCE DESCRIPTION: SEQ ID NO:26:

AATTCGGCTC GGAGACGGTC GTGTCGGCGG AGGCCGGCCC    40

(2) INFORMATION FOR SEQ ID NO:27:

(i) SEQUENCE CHARACTERISTICS:
        (A) LENGTH: 15 amino acids (B) TYPE: amino acid
(D) TOPOLOGY: unknown (ii) MOLECULE TYPE: peptide (xi) SEQUENCE DESCRIPTION: SEQ ID NO:27:

Ala Gly Pro Ala Ser Ala Asp Thr Thr Val Ser Glu Pro Asp Pro
 -5              -1                   5

(2) INFORMATION FOR SEQ ID NO:28:

(i) SEQUENCE CHARACTERISTICS:
    (A) LENGTH: 46 base pairs
    (B) TYPE: nucleic acid
    (C) STRANDEDNESS: both
    (D) TOPOLOGY: linear (ii) MOLECULE TYPE: Other nucleic acid
    (A) DESCRIPTION: synthetic DNA (xi) SEQUENCE DESCRIPTION: SEQ ID NO:28:

GGCCGGGCCG GCCTCCGCCG ACACGACCGT CTCCGAGCCC GACCCG    46

(2) INFORMATION FOR SEQ ID NO:29:

(i) SEQUENCE CHARACTERISTICS:
    (A) LENGTH: 46 base pairs
    (B) TYPE: nucleic acid
    (C) STRANDEDNESS: both
    (D) TOPOLOGY: linear (ii) MOLECULE TYPE: Other nucleic acid
    (A) DESCRIPTION: synthetic DNA (iv) ANTI-SENSE: YES (ix) FEATURE:
    (A) NAME/KEY: misc_feature
    (B) LOCATION: 5..46
    (D) OTHER INFORMATION: /note="Sequence ID No. 29 is
        complementary to Sequence ID No. 28 at positions
        5-44 of Sequence ID No. 28."

(xi) SEQUENCE DESCRIPTION: SEQ ID NO:29:

AATTCGGGTC GGGCTCGGAG ACGGTCGTGT CGGCGGAGGC CGGCCC    46

(2) INFORMATION FOR SEQ ID NO:30:

(i) SEQUENCE CHARACTERISTICS:
    (A) LENGTH: 15 amino acids
    (B) TYPE: amino acid
    (D) TOPOLOGY: unknown (ii) MOLECULE TYPE: peptide (xi) SEQUENCE DESCRIPTION: SEQ ID NO:30:

Ala Gly Pro Ala Ser Ala Asp Thr Thr Val Ser Glu Pro Ala Pro
 -5              -1                   5

(2) INFORMATION FOR SEQ ID NO:31:

(i) SEQUENCE CHARACTERISTICS:
    (A) LENGTH: 46 base pairs
    (B) TYPE: nucleic acid
    (C) STRANDEDNESS: both
    (D) TOPOLOGY: unknown (ii) MOLECULE TYPE: Other nucleic acid
    (A) DESCRIPTION: synthetic DNA (xi) SEQUENCE DESCRIPTION: SEQ ID NO:31:

GGCCGGGCCG GCCTCCGCCG ACACGACCGT CTCCGAGCCC GCACCG    46

( 2 ) INFORMATION FOR SEQ ID NO:32:

( i ) SEQUENCE CHARACTERISTICS:
        ( A ) LENGTH: 46 base pairs
        ( B ) TYPE: nucleic acid
        ( C ) STRANDEDNESS: both
        ( D ) TOPOLOGY: linear ( i i ) MOLECULE TYPE: Other nucleic acid
        ( A ) DESCRIPTION: synthetic DNA ( i v ) ANTI-SENSE: YES ( i x ) FEATURE:
        ( A ) NAME/KEY: misc_feature
        ( B ) LOCATION: 5..46
        ( D ) OTHER INFORMATION: /note="Sequence ID No. 32 is
        complementary to Sequence ID No. 31 at positions
        5-43 of Sequence ID No. 31."

( x i ) SEQUENCE DESCRIPTION: SEQ ID NO:32:

```
AATTCGGTGC GGGCTCGGAG ACGGTCGTGT CGGCGGAGGC CGGCCC                    46
```

( 2 ) INFORMATION FOR SEQ ID NO:33:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

```
Asn Ser Asn Gly Lys
1               5
```

( 2 ) INFORMATION FOR SEQ ID NO:34:

( i ) SEQUENCE CHARACTERISTICS:
        ( A ) LENGTH: 36 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:34:

```
Asn Ser Asn Gly Arg Phe Val Asn Gln His Leu Cys Gly Ser His Leu
1               5                   10                  15

Val Glu Ala Leu Tyr Leu Val Cys Gly Glu Arg Gly Phe Phe Tyr Thr
                20                  25                  30

Pro Lys Thr Arg
            35
```

( 2 ) INFORMATION FOR SEQ ID NO:35:

( i ) SEQUENCE CHARACTERISTICS:
        ( A ) LENGTH: 108 base pairs
        ( B ) TYPE: nucleic acid
        ( C ) STRANDEDNESS: double
        ( D ) TOPOLOGY: linear ( i i ) MOLECULE TYPE: Other nucleic acid
        ( A ) DESCRIPTION: synthetic DNA ( x i ) SEQUENCE DESCRIPTION: SEQ ID NO:35:

```
AATTCGAACG GCCGCTTCGT CAACCAGCAC CTGTGCGGCT CGCACCTCGT GGAGGCCCTC     60

TACCTGGTGT GCGGGGAGCG CGGCTTCTTC TACACCCCCA AGACCCGC                  108
```

( 2 ) INFORMATION FOR SEQ ID NO:36:

( i ) SEQUENCE CHARACTERISTICS:
    ( A ) LENGTH: 86 base pairs
    ( B ) TYPE: nucleic acid
    ( C ) STRANDEDNESS: double
    ( D ) TOPOLOGY: linear ( i i ) MOLECULE TYPE: Other nucleic acid
    ( A ) DESCRIPTION: synthetic DNA ( x i ) SEQUENCE DESCRIPTION: SEQ ID NO:36:

```
CTGCAGTGAT CAGGGGGACC CTTGTGCGAA TTTCCGTTAC GGGTTTGGGT GGTAGGGACG        60
CACCCGAAGA GGAGGCCCCA GCATGC                                             86
```

( 2 ) INFORMATION FOR SEQ ID NO:37:

( i ) SEQUENCE CHARACTERISTICS:
    ( A ) LENGTH: 15 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:37:

```
Asn  Ser  Ala  Arg  Phe  Val  Asn  Gln  His  Leu  Cys  Gly  Ser  His  Leu
1                  5                   10                          15
```

( 2 ) INFORMATION FOR SEQ ID NO:38:

( i ) SEQUENCE CHARACTERISTICS:
    ( A ) LENGTH: 45 base pairs
    ( B ) TYPE: nucleic acid
    ( C ) STRANDEDNESS: both
    ( D ) TOPOLOGY: linear ( i i ) MOLECULE TYPE: Other nucleic acid
    ( A ) DESCRIPTION: synthetic DNA ( x i ) SEQUENCE DESCRIPTION: SEQ ID NO:38:

```
AATTCGGCCC GCTTCGTCAA CCAGCACCTG TGCGGCTCGC ACCTC                        45
```

( 2 ) INFORMATION FOR SEQ ID NO:39:

( i ) SEQUENCE CHARACTERISTICS:
    ( A ) LENGTH: 74 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:39:

```
Asp  Thr  Thr  Val  Ser  Glu  Pro  Ala  Pro  Ser  Cys  Val  Thr  Leu  Tyr  Gln
1                  5                   10                          15

Ser  Trp  Arg  Tyr  Ser  Gln  Ala  Asp  Asn  Gly  Cys  Ala  Glu  Thr  Val  Thr
                20                  25                          30

Val  Lys  Val  Val  Tyr  Glu  Asp  Asp  Thr  Glu  Gly  Leu  Cys  Tyr  Ala  Val
            35                  40                          45

Ala  Pro  Gly  Gln  Ile  Thr  Thr  Val  Gly  Asp  Gly  Tyr  Ile  Gly  Ser  His
         50                     55                       60

Gly  His  Ala  Arg  Tyr  Leu  Ala  Arg  Cys  Leu
65                      70
```

( 2 ) INFORMATION FOR SEQ ID NO:40:

( i ) SEQUENCE CHARACTERISTICS:
    ( A ) LENGTH: 225 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:40:

| | | | | | |
|---|---|---|---|---|---|
| GACACGACCG | TCTCCGAGCC | CGCACCCTCC | TGCGTGACGC | TCTACCAGAG | CTGGCGGTAC | 60
| TCACAGGCCG | ACAACGGCTG | TGCCGAGACG | GTGACCGTGA | AGGTCGTCTA | CGAGGACGAC | 120
| ACCGAAGGCC | TGTGCTACGC | CGTCGCACCG | GGCCAGATCA | CCACCGTCGG | CGACGGCTAC | 180
| ATCGGCTCGC | ACGGCCACGC | GCGCTACCTG | GCTCGCTGCC | TTTAG | | 225

( 2 ) INFORMATION FOR SEQ ID NO:41:

( i ) SEQUENCE CHARACTERISTICS:
        ( A ) LENGTH: 290 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:41:

| | | | | | |
|---|---|---|---|---|---|
| AATTCTGCAA | GATTTGTGAA | CCAGCACCTG | TGCGGCTCCC | ACCTAGTGGA | AGCTCTCTAC | 60
| CTGGTGTGCG | GGGAGCGAGG | CTTCTTCTAC | ACACCCAAGA | CCCGCCGGGA | GGCAGAGGAC | 120
| CCTCAGGTGG | GGCAGGTGGA | GCTGGGCGGG | GGCCCTGGCG | CAGGCAGCCT | GCAGCCCTTG | 180
| GCGCTGGAGG | GGTCCCTGCA | GAAGCGCGGC | ATCGTGGAGC | AGTGCTGCAC | CAGCATCTGC | 240
| TCCCTCTACC | AGCTGGAGAA | CTACTGCAAC | TAATAGTCGA | CCTGCAGCCA | | 290

( 2 ) INFORMATION FOR SEQ ID NO:42:

( i ) SEQUENCE CHARACTERISTICS:
        ( A ) LENGTH: 290 base pairs
        ( B ) TYPE: nucleic acid
        ( C ) STRANDEDNESS: both
        ( D ) TOPOLOGY: linear ( i i ) MOLECULE TYPE: DNA (genomic)

( i v ) ANTI-SENSE: YES ( i x ) FEATURE:
        ( A ) NAME/KEY: misc_feature
        ( B ) LOCATION: 5..290
        ( D ) OTHER INFORMATION: /note="Sequence ID No. 42 is
        complementary to Sequence ID No. 41 at positions
        5-290 of Sequence ID No. 41."

( x i ) SEQUENCE DESCRIPTION: SEQ ID NO:42:

| | | | | | |
|---|---|---|---|---|---|
| AGCTTGGCTG | CAGGTCGACT | ATTAGTTGCA | GTAGTTCTCC | AGCTGGTAGA | GGGAGCAGAT | 60
| GCTGGTGCAG | CACTGCTCCA | CGATGCCGCG | CTTCTGCAGG | GACCCCTCCA | GCGCCAAGGG | 120
| CTGCAGGCTG | CCTGCGCCAG | GGCCCCCGCC | CAGCTCCACC | TGCCCCACCT | GAGGGTCCTC | 180
| TGCCTCCCGG | CGGGTCTTGG | GTGTGTAGAA | GAAGCCTCGC | TCCCCGCACA | CCAGGTAGAG | 240
| AGCTTCCACT | AGGTGGGAGC | CGCACAGGTG | CTGGTTCACA | ATCTTGCAG | | 290

( 2 ) INFORMATION FOR SEQ ID NO:43:

( i ) SEQUENCE CHARACTERISTICS:
        ( A ) LENGTH: 90 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:43:

| Asn | Ser | Ala | Arg | Phe | Val | Asn | Gln | His | Leu | Cys | Gly | Ser | His | Leu | Val |
|---|---|---|---|---|---|---|---|---|---|---|---|---|---|---|---|
| 1 | | | | 5 | | | | | 10 | | | | | 15 | |

|      |     |     |     |     |     |     |     |     |     |     |     |     |     |
|------|-----|-----|-----|-----|-----|-----|-----|-----|-----|-----|-----|-----|-----|
| Glu  | Ala | Leu | Tyr | Leu | Val | Cys | Gly | Glu | Arg | Gly | Phe | Phe | Tyr | Thr | Pro |
|      |     |     | 20  |     |     |     |     | 25  |     |     |     |     |     | 30  |     |
| Lys  | Thr | Arg | Arg | Glu | Ala | Glu | Asp | Pro | Gln | Val | Gly | Gln | Val | Glu | Leu |
|      |     | 35  |     |     |     |     | 40  |     |     |     |     | 45  |     |     |     |
| Gly  | Gly | Gly | Pro | Gly | Ala | Gly | Ser | Leu | Gln | Pro | Leu | Ala | Leu | Glu | Gly |
|      | 50  |     |     |     |     | 55  |     |     |     |     | 60  |     |     |     |     |
| Ser  | Leu | Gln | Lys | Arg | Gly | Ile | Val | Glu | Gln | Cys | Cys | Thr | Ser | Ile | Cys |
| 65   |     |     |     |     | 70  |     |     |     |     | 75  |     |     |     |     | 80  |
| Ser  | Leu | Tyr | Gln | Leu | Glu | Asn | Tyr | Cys | Asn |     |     |     |     |     |     |
|      |     |     | 85  |     |     |     |     |     | 90  |     |     |     |     |     |     |

( 2 ) INFORMATION FOR SEQ ID NO:44:

( i ) SEQUENCE CHARACTERISTICS:
        ( A ) LENGTH: 57 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:44:

| Asn | Ser | Asn | Gly | Lys | Phe | Val | Asn | Gln | His | Leu | Cys | Gly | Ser | His | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Val | Glu | Ala | Leu | Tyr | Leu | Val | Cys | Gly | Glu | Arg | Gly | Phe | Phe | Tyr | Thr |
|     |     |     | 20  |     |     |     |     | 25  |     |     |     |     |     | 30  |     |
| Pro | Lys | Thr | Lys | Gly | Ile | Val | Glu | Gln | Cys | Cys | Thr | Ser | Ile | Cys | Ser |
|     |     | 35  |     |     |     |     | 40  |     |     |     |     | 45  |     |     |     |
| Leu | Tyr | Gln | Leu | Glu | Asn | Tyr | Cys | Asn |     |     |     |     |     |     |     |
|     |     | 50  |     |     |     | 55  |     |     |     |     |     |     |     |     |     |

( 2 ) INFORMATION FOR SEQ ID NO:45:

( i ) SEQUENCE CHARACTERISTICS:
        ( A ) LENGTH: 192 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:45:

```
AATTCGAACG GCAAGTTCGT CAACCAGCAC CTGTGCGGCT CGCACCTCGT GGAGGCCCTC      60
TACCTGGTGT GCGGGGAGCG CGGCTTCTTC TACACCCCCA AGACCAAGGG CATCGTGGAG     120
CAGTGCTGTA CGTCCATCTG CTCCCTCTAC AGCTCGAGA  ACTACTGCAA CTAGTAAGTC     180
GACCTGCAGC CA                                                         192
```

( 2 ) INFORMATION FOR SEQ ID NO:46:

( i ) SEQUENCE CHARACTERISTICS:
        ( A ) LENGTH: 192 base pairs
        ( B ) TYPE: nucleic acid
        ( C ) STRANDEDNESS: both
        ( D ) TOPOLOGY: linear ( i i ) MOLECULE TYPE: DNA (genomic)

( i x ) FEATURE:
        ( A ) NAME/KEY: misc_feature
        ( B ) LOCATION: 5..192
        ( D ) OTHER INFORMATION: /note="Sequence ID No. 46 is
        complementary to Sequence ID No. 45 at positions
        5-192 of Sequence ID No. 45."

( x i ) SEQUENCE DESCRIPTION: SEQ ID NO:46:

```
AGCTTGGCTG CAGGTCGACT TACTAGTTGC AGTAGTTCTC GAGCTGGTAG AGGGAGCAGA      60
```

```
TGGACGTACA  GCACTGCTCC  ACGATGCCCT  TGGTCTTGGG  GGTGTAGAAG  AAGCCGCGCT          120

CCCCGCACAC  CAGGTAGAGG  GCCTCCACGA  GGTGCGAGCC  GCACAGGTGC  TGGTTGACGA          180

ACTTGCCGTT  CG                                                                  192
```

( 2 ) INFORMATION FOR SEQ ID NO:47:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:47:

```
CGATAAACCG  ATACAATTAA  AGGCTCCTTT  TGGAGCCTTT  TTTTTGGAG  ATTTTCAACG           60

TGGATC                                                                          66
```

( 2 ) INFORMATION FOR SEQ ID NO:48:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Region
        ( B ) LOCATION: 8
        ( D ) OTHER INFORMATION: /note="Xaa represents a
        hydrophobic region comprising 10 to 25 amino
        acids."

( x i ) SEQUENCE DESCRIPTION: SEQ ID NO:48:

```
Met  Arg  Val  Arg  Ala  Leu  Arg  Xaa  Ala  Ser  Ala
 1              5                        10
```